United States Patent
Yun et al.

(10) Patent No.: US 9,448,190 B2
(45) Date of Patent: *Sep. 20, 2016

(54) HIGH BRIGHTNESS X-RAY ABSORPTION SPECTROSCOPY SYSTEM

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/636,994

(22) Filed: Mar. 3, 2015

(65) Prior Publication Data

US 2015/0357069 A1    Dec. 10, 2015

Related U.S. Application Data

(60) Provisional application No. 62/008,856, filed on Jun. 6, 2014, provisional application No. 62/086,132, filed on Dec. 1, 2014, provisional application No. 62/117,062, filed on Feb. 17, 2015.

(51) Int. Cl.
*H01J 35/08* (2006.01)
*G01N 23/207* (2006.01)
(Continued)

(52) U.S. Cl.
CPC ........ *G01N 23/2076* (2013.01); *G01N 23/063* (2013.01); *H01J 35/08* (2013.01);
(Continued)

(58) Field of Classification Search
CPC ............... H01J 35/08; H01J 2235/087; H01J 2235/088; H01J 2235/086; H01J 2235/081; H01J 2235/068; H01J 2235/08; H01J 35/00; G21K 1/067; G21K 2201/062; G21K 2201/06; G21K 5/10; G21K 1/02; G21K 1/06; G03F 7/70958; G03F 7/70191; G01N 2223/076; G01N 23/2076
See application file for complete search history.

(56) References Cited

U.S. PATENT DOCUMENTS

| 1,203,495 A | 10/1916 | Coolidge |
| 1,211,092 A | 1/1917 | Coolidge |

(Continued)

FOREIGN PATENT DOCUMENTS

| EP | 0432568 A2 | 6/1991 |
| EP | 0751533 A1 | 1/1997 |

(Continued)

OTHER PUBLICATIONS

Rovezzi, Study of the local order around magnetic impurities in semiconductors for spintronics, Dec. 23, 2009, PhD dissertation, Condensed Matter, Universite Joseph-Fourier—Grenoble I, 165 total pages.*

(Continued)

*Primary Examiner* — David J Makiya
*Assistant Examiner* — John Corbett
(74) *Attorney, Agent, or Firm* — Franklin Schellenberg

(57) ABSTRACT

This disclosure presents systems for x-ray absorption fine structure (XAFS) measurements that have x-ray flux and flux density several orders of magnitude greater than existing compact systems. These are useful for laboratory or field applications of x-ray absorption near-edge spectroscopy (XANES) or extended x-ray fine absorption structure (EXFAS) spectroscopy. The higher brightness is achieved by using designs for x-ray targets that comprise a number of aligned microstructures of x-ray generating materials fabricated in close thermal contact with a substrate having high thermal conductivity. This allows for bombardment with higher electron density and/or higher energy electrons, leading to greater x-ray brightness and high flux. The high brightness x-ray source is then coupled to an x-ray reflecting optical system to collimate the x-rays, and a monochromator, which selects the exposure energy. Absorption spectra of samples using the high flux monochromatic x-rays can be made using standard detection techniques.

30 Claims, 13 Drawing Sheets

(51) Int. Cl.
 *H01J 35/14* (2006.01)
 *G01N 23/06* (2006.01)
(52) U.S. Cl.
 CPC ........ *H01J 35/14* (2013.01); *G21K 2201/061* (2013.01); *G21K 2201/062* (2013.01); *G21K 2201/064* (2013.01); *H01J 2235/081* (2013.01); *H01J 2235/086* (2013.01)

(56) References Cited

U.S. PATENT DOCUMENTS

| | | |
|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,227,112 A | 10/1980 | Waugh et al. |
| 4,266,138 A | 5/1981 | Nelson, Jr. et al. |
| 4,523,327 A | 6/1985 | Eversole |
| 4,573,186 A | 2/1986 | Reinhold |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,148,462 A | 9/1992 | Spitsyn et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,729,583 A | 3/1998 | Tang et al. |
| 5,768,339 A * | 6/1998 | O'Hara ........................ 378/147 |
| 5,772,903 A | 6/1998 | Hirsch |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,377,660 B1 | 4/2002 | Ukita et al. |
| 6,381,303 B1 | 4/2002 | Vu et al. |
| 6,430,254 B2 | 8/2002 | Wilkins |
| 6,456,688 B1 | 9/2002 | Taguchi et al. |
| 6,463,123 B1 | 10/2002 | Korenev |
| 6,487,272 B1 | 11/2002 | Kutsuzawa |
| 6,560,313 B1 | 5/2003 | Harding et al. |
| 6,560,315 B1 | 5/2003 | Price et al. |
| 6,707,883 B1 | 3/2004 | Tiearney, Jr. et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 7,003,077 B2 | 2/2006 | Jen et al. |
| 7,057,187 B1 | 6/2006 | Yun et al. |
| 7,079,625 B2 | 7/2006 | Lenz |
| 7,095,822 B1 | 8/2006 | Yun |
| 7,119,953 B2 | 10/2006 | Yun et al. |
| 7,130,375 B1 | 10/2006 | Yun et al. |
| 7,170,969 B1 | 1/2007 | Yun et al. |
| 7,183,547 B2 | 2/2007 | Yun et al. |
| 7,215,736 B1 | 5/2007 | Wang et al. |
| 7,215,741 B2 | 5/2007 | Ukita |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,330,533 B2 | 2/2008 | Sampayon |
| 7,346,148 B2 | 3/2008 | Ukita |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun et al. |
| 7,412,024 B1 | 8/2008 | Yun et al. |
| 7,412,131 B2 | 8/2008 | Lee et al. |
| 7,414,787 B2 | 8/2008 | Yun et al. |
| 7,443,953 B1 | 10/2008 | Yun et al. |
| 7,499,521 B2 | 3/2009 | Wang et al. |
| 7,522,707 B2 | 4/2009 | Steinlage et al. |
| 7,529,343 B2 | 5/2009 | Safai et al. |
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,601,399 B2 | 10/2009 | Barnola et al. |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Wu et al. |
| 7,800,072 B2 | 9/2010 | Yun et al. |
| 7,813,475 B1 | 10/2010 | Wu et al. |
| 7,817,777 B2 | 10/2010 | Baumann et al. |
| 7,864,426 B2 | 1/2011 | Yun et al. |
| 7,873,146 B2 | 1/2011 | Okunuki et al. |
| 7,889,844 B2 | 2/2011 | Okunuki et al. |
| 7,914,693 B2 | 3/2011 | Jeong et al. |
| 7,920,676 B2 | 4/2011 | Yun et al. |
| 7,929,667 B1 | 4/2011 | Zhuang et al. |
| 7,974,379 B1 | 7/2011 | Case et al. |
| 7,991,120 B2 | 8/2011 | Okunuki et al. |
| 8,036,341 B2 | 10/2011 | Lee |
| 8,068,579 B1 | 11/2011 | Yun et al. |
| 8,094,784 B2 | 1/2012 | Morton |
| 8,139,716 B2 | 3/2012 | Okunuki et al. |
| 8,208,603 B2 | 6/2012 | Sato |
| 8,243,884 B2 | 8/2012 | Rödhammer et al. |
| 8,306,184 B2 | 11/2012 | Chang et al. |
| 8,353,628 B1 | 1/2013 | Yun et al. |
| 8,360,640 B2 | 1/2013 | Reinhold |
| 8,406,378 B2 | 3/2013 | Wang et al. |
| 8,416,920 B2 | 4/2013 | Okumura et al. |
| 8,422,633 B2 | 4/2013 | Lantz et al. |
| 8,422,637 B2 | 4/2013 | Okunuki et al. |
| 8,509,386 B2 | 8/2013 | Lee et al. |
| 8,520,803 B2 | 8/2013 | Behling |
| 8,526,575 B1 | 9/2013 | Lyon et al. |
| 8,553,843 B2 | 10/2013 | Drory |
| 8,559,597 B2 | 10/2013 | Chen et al. |
| 8,602,648 B1 | 12/2013 | Jacobsen et al. |
| 8,666,024 B2 | 3/2014 | Okunuki et al. |
| 8,699,667 B2 | 4/2014 | Steinlage et al. |
| 8,735,844 B1 * | 5/2014 | Khaykovich et al. ..... 250/390.1 |
| 8,737,565 B1 | 5/2014 | Lyon et al. |
| 8,744,048 B2 | 6/2014 | Lee et al. |
| 8,831,175 B2 | 9/2014 | Silver et al. |
| 8,831,179 B2 | 9/2014 | Adler et al. |
| 8,861,682 B2 | 10/2014 | Okunuki et al. |
| 8,995,622 B2 | 3/2015 | Adler et al. |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,129,715 B2 | 9/2015 | Adler et al. |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0282300 A1 | 12/2005 | Yun et al. |
| 2007/0071174 A1 | 3/2007 | Hebert et al. |

(56) References Cited

U.S. PATENT DOCUMENTS

| | | | |
|---|---|---|---|
| 2007/0108387 A1 | 5/2007 | Yun et al. | |
| 2007/0110217 A1 | 5/2007 | Ukita | |
| 2007/0248215 A1* | 10/2007 | Ohshima | G01N 23/04 378/143 |
| 2008/0089484 A1 | 4/2008 | Reinhold | |
| 2008/0094694 A1 | 4/2008 | Yun et al. | |
| 2008/0159707 A1 | 7/2008 | Lee et al. | |
| 2008/0170662 A1 | 7/2008 | Reinhold | |
| 2008/0170668 A1 | 7/2008 | Kruit et al. | |
| 2008/0181363 A1 | 7/2008 | Fenter et al. | |
| 2008/0240344 A1 | 10/2008 | Reinhold | |
| 2009/0154640 A1 | 6/2009 | Baumann et al. | |
| 2009/0316860 A1 | 12/2009 | Okunuki et al. | |
| 2010/0040202 A1 | 2/2010 | Lee | |
| 2010/0141151 A1 | 6/2010 | Reinhold | |
| 2010/0272239 A1* | 10/2010 | Lantz et al. | 378/145 |
| 2011/0026680 A1* | 2/2011 | Sato | 378/119 |
| 2011/0058655 A1 | 3/2011 | Okumura et al. | |
| 2011/0135066 A1 | 6/2011 | Behling | |
| 2012/0163547 A1 | 6/2012 | Lee et al. | |
| 2012/0269323 A1 | 10/2012 | Adler et al. | |
| 2012/0269324 A1 | 10/2012 | Adler | |
| 2012/0269325 A1 | 10/2012 | Adler et al. | |
| 2012/0269326 A1 | 10/2012 | Adler et al. | |
| 2013/0195246 A1* | 8/2013 | Tamura et al. | 378/62 |
| 2013/0259207 A1 | 10/2013 | Omote et al. | |
| 2013/0308754 A1 | 11/2013 | Yamazaki et al. | |
| 2014/0037052 A1 | 2/2014 | Adler | |
| 2014/0064445 A1 | 3/2014 | Adler | |
| 2014/0072104 A1 | 3/2014 | Jacobsen et al. | |
| 2014/0105363 A1 | 4/2014 | Chen et al. | |
| 2014/0177800 A1 | 6/2014 | Sato et al. | |
| 2014/0185778 A1 | 7/2014 | Lee et al. | |
| 2014/0211919 A1 | 7/2014 | Ogura et al. | |
| 2014/0369469 A1 | 12/2014 | Ogura et al. | |
| 2015/0030127 A1 | 1/2015 | Aoki et al. | |
| 2015/0043713 A1 | 2/2015 | Chen | |

FOREIGN PATENT DOCUMENTS

| | | |
|---|---|---|
| EP | 1028451 A1 | 8/2000 |
| JP | 2000-306533 A | 11/2000 |
| JP | 2007-265981 A | 10/2007 |
| JP | 2007-311185 A | 11/2007 |
| JP | 2013-157269 A | 8/2013 |
| JP | 2013-160637 A | 8/2013 |
| JP | 2013-239317 A | 11/2013 |
| WO | 95/06952 A1 | 3/1995 |
| WO | 98/11592 A1 | 3/1998 |
| WO | 02/39792 A2 | 5/2002 |
| WO | 03/081631 A2 | 10/2003 |
| WO | 2005/109969 A2 | 11/2005 |
| WO | 2006/096052 A2 | 9/2006 |
| WO | 2009/098027 A1 | 8/2009 |
| WO | 2013/118593 A1 | 8/2013 |
| WO | 2013/168468 A1 | 11/2013 |

OTHER PUBLICATIONS

Baron et al., A compact optical design for Bragg reflections near backscattering, 2001, Journal of Synchrotron Radiation, vol. 8, pp. 1127-1130.*

Li et al., Source-optic-crystal optimization for compact monochromatic imaging, 2004, SPIE vol. 5537, pp. 105-114.*

X-ray-optics.de, http://www.x-ray-optics.de/index.php?option=com_content&view=article&id=59&Itemid=71.*

Masushita, X-ray monochromators, Nov. 4, 2009, Cheiron School 2009 lecture, 70 pages located at http://cheiron2009.spring8.or.jp/lecture.html.*

Oji et al., Automatic XAFS measurement system developed at BL14B2 in SPring-8, Available online Nov. 15, 2011, Journal of Synchrotron Radiation, vol. 19, pp. 54-59.*

Honma et al., Full-automatic XAFS Measurement System of the Engineering Science Research II beamline BL14B2 at Spring-8, 2011, AIP Conference Proceedings 1234, pp. 13-16.*

Arndt et al., Focusing Mirrors for Use with Microfocus X-ray Tubes, 1998, Journal of Applied Crystallography, vol. 31, pp. 733-741.*

W.C. Röntgen, Ueber eine neue Art von Strahlen (Würzburg Verlag, Würzburg, Germany, 1896) also, in English, "On a New Kind of Rays," Nature vol. 53 (Jan. 23 1896), pp. 274-276.

N. Langhoff & A. Simionovici, "X-ray Sources", Ch. 2 of "Handbook of Practical X-Ray Fluorescence Analysis", B. Beckhoff et al., eds. (Springer, Berlin Heidelberg New York, 2006), pp. 33-82.

Jens Als-Nielsen & Des McMorrow "X-rays and their interaction with matter", and "Sources", Ch.1 & 2 of "Elements of Modern X-ray Physics, Second Edition" (John Wiley & Sons Ltd, Chichester, West Sussex, UK, 2011), pp. 1-67.

P.J. Potts, "Electron Probe Microanalysis", Ch. 10 of "A Handbook of Silicate Rock Analysis" (Springer Science + Business Media, New York, 1987), pp. 326-382 (equation quoted from p. 336).

J. G. Chervenak & A. Liuzzi, "Experimental thick-target bremsstrahlung spectra from electrons in the range 10 to 30 keV", Phys. Rev. A vol. 12 (1975), pp. 26-33.

P.D. Prewitt et al., "FIB Repair of 5X Reticles and Effects on IC Quality", in Integrated Circuit Metrology, Inspection, and Process Control VII, Proc. SPIE vol. 1926 (1993), pp. 517-526.

P.D. Prewitt et al., "Gallium Staining in FIB Repair of Photomasks", Microelectronic Engineering vol. 21 (1993), pp. 191-196.

P.D. Prewitt and G.M. Sundaram,"Focused ion beam repair: staining of photomasks and reticles" J. Phys. D Appl. Phys. vol. 26 (1993), pp. 1135-1137.

Guifu Ding et al., "Reactive Ion Etching of CVD Diamond Films for MEMS Applications", in Micromachining and Microfabrication, Proc. SPIE vol. 4230 (2000) pp. 224-230.

Qiaoqin Yang et al., "Analysis of Intrinsic Stress in Diamond Films by X-ray Diffraction", in Advances in X-ray Analysis, vol. 43 (2000) pp. 151-156.

X.D. Wang et al., "Precise patterning of diamond films for MEMS application" Journal of Materials Processing Technology vol. 127 (2002), pp. 230-233.

Heinz-Dieter Nuhn, "From storage rings to free electron lasers for hard x-rays", J. Phys.: Condens. Matter vol. 16 (2004), pp. S3413-S34121.

Shigehiko Yamamoto, "Fundamental physics of vacuum electron sources", Reports on Progress in Physics vol. 69, (2006), pp. 181-232.

"Diamond", Section 10.4.2 of Christian A. Zorman and Mehran Mehregany, "Material Aspects of Micro-Nanoelectromechanical Systems", Chapter 10 of Springer Handbook of Nanotechnology, 2nd Ed., Barat Bushan, ed. (Springer Science + Business Media, Inc., New York, 2007) pp. 312-314.

M. Otendal T. Tuohimaa, U. Vogt & H.M. Hertz, "A 9 keV electron-impact liquid-gallium-jet x-ray source", Rev. Sci. Instrum. vol. 79 (2008): 016102.

Aamir Ihsan, Sung Hwan Heo & Sung Oh Cho , "A microfocus X-ray tube based on a microstructured X-ray target", Nuclear Instruments and Methods in Physics Research B vol. 267 (2009), pp. 3566-3573.

D. Gonzales, B. Cavness & S. Williams, "Angular distribution of thick-target bremsstrahlung produced by electrons with initial energies ranging from 10 to 20 keV incident on Ag", Phys. Rev. A vol. 84 (2011): 052726.

D. Gonzales & S. Williams, "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.

Jicheng Zhang et al., "Fabrication of Diamond Microstructures by Using Dry and Wet Etching Methods", Plasma Science and Technology vol. 15(6) (Jun. 2013), pp. 552-554.

Takayoshi Shimura et al., "Hard x-ray phase contrast imaging using a tabletop Talbot-Lau interferometer with multiline embedded x-ray targets", Opt. Lett. vol. 38(2) (2013) pp. 157-159.

(56) References Cited

OTHER PUBLICATIONS

Alireza Nojeh, "Carbon Nanotube Electron Sources: From Electron Beams to Energy Conversion and Optophononics", ISRN Nanomaterials vol. 2014 (2014): 879827.

Yasuo Udagawa, "An Introduction to In-House EXAFS Facilities" The Rigaku Journal, vol. 6 (1) (1989), pp. 20-27.

C. Malgrange, "X-ray Optics for Synchrotron Radiation" ACTA Physica Polinica A, vol. 82(1) (1992), pp. 13-32.

Yasuo Udagawa, "An Introduction to X-ray Absorption Fine Structure", The Rigaku Journal, vol. 11(2) (1994), pp. 30-39.

Alfred Q.R. Baron et al., "A compact optical design for Bragg reflections near backscattering", J. Synchrotron Rad. vol. 8 (2001), pp. 1127-1130.

P. Lechner et al., "Silicon drift detectors for high count rate X-ray spectroscopy at room temperature", Nuclear Instruments and Methods, vol. 458A, (2001), pp. 281-287.

Matthew Newville, "Fundamentals of XAFS" (Univ. of Chicago, Chicago, IL, Jul. 23, 2004).

Kouichi Tsuji, Jasna Injuk & Rene Van Grieken, "X-Ray Spectrometry: Recent Technological Advances" (John Wiley & Sons Ltd, Chichester, West Sussex, UK, 2004), Chapters 1-7.

J. A. Maj et al. "Etching methods for improving surface imperfections of diamonds used for x-ray monochromators" Adv. X-ray Anal. vol. 48 (2005), pp. 176-182.

Tirandai Hemraj-Benny et al., "Near-Edge X-ray Absorption Fine Structure Spectroscopy as a Tool for Investigating Nanomaterials", Small vol. 2(1), (2006) pp. 26-35.

Markus Scholz, "X-ray Tubes and Monochromators", Technical Workshop EPIV, Universität Würzburg (2007); 41 slides, available at <http://www.physik.uni-wuerzburg.de/EP4/teaching/WS2007_08/technikseminar/xraytubesws0708.pdf>.

J. Hrdý and J. Hrdá, "Diffractive-Refractive Optics: X-ray Crystal Monochromators with Profiled Diffracting Surfaces", Ch. 26. of "Modern Developments in X-Ray and Neutron Optics", A. Erko et al., eds. (Springer, Berlin Heidelberg New York, 2008).

T. Matsushita, "X-ray monochromators", Slide Presentation from Photon Factory, Tsukuba, Japan, 70 slides, (Cheiron School 2009, SPring-8, Japan, Nov. 2009) available at < http://cheiron2009.spring8.or.jp/images/PDF/Lecture/X-ray_Monochromator_T_Matsushita.pdf >.

Mauro Rovezzi, "Study of the local order around magnetic impurities in semiconductors for spintronics", PhD dissertation, Condensed Matter. Université Joseph-Fourier—Grenoble I, 2009. English. <tel-00442852>.

Jens Als-Nielsen & Des McMorrow "Photoelectric Absorption", Ch. 7 of "Elements of Modern X-ray Physics, Second Edition", (John Wiley & Sons Ltd, Chichester, West Sussex, UK, 2011).

Paul Kirkpatrick & A.V. Baez, "Formation of Optical Images by X-Rays" J. Opt. Soc. Am. vol. 38 (Sep. 1948), pp. 766-774.

Hans Wolter, "Spiegelsysteme streifenden Einfalls als abbildende Optiken für Röntgenstrahlen" [Grazing-Incidence Reflector Systems as Imaging Optics for X-rays] Annalen der Physik vol. 445, Issue 1-2 (1952), pp. 94-114.

Janos Kirz, "Phase zone plates for x rays and the extreme uv" J. Opt. Soc. Am. vol. 64 (Mar. 1974) pp. 301-309.

Troy W. Barbee Jr. "Multilayers for x-ray optics" Opt. Eng. vol. 25 (Aug. 1986) pp. 898-915.

Malcolm R. Howells, "Mirrors for Synchrotron-Radiation Beamlines", Publication LBL-34750 (Larrence Berkeley Laboratory, Berkeley, CA, Sep. 1993).

David X. Balaic & Keith A. Nugent, "X-ray optics of tapered capillaries" Appl. Opt. vol. 34 (Nov. 1995), pp. 7263-7272.

Muradin A. Kumakhov, "X-ray Capillary Optics. History of Development and Present Status" in Kumakhov Optics and Application, Proc. SPIE vol. 4155 (2000), pp. 2-12.

Carolyn A. MacDonald & Walter M. Gibson, "An Introduction to X-ray and Neutron Optics", Ch. 19 of "Handbook of Optics vol. III, 2nd Ed." (McGraw Hill, New York, 2001).

B. Lengeler, C. Schroer, J. Tümmler, B. Benner, A. Snigirev & I. Snigireva, "Refractive X-ray Optics", Ch. 20 of "Handbook of Optics vol. III, 2nd Ed." (McGraw Hill, New York, 2001).

Malcolm R. Howells, "Gratings and Monochromators in the VUV and Soft X-ray Spectral Region" Ch. 21 of "Handbook of Optics vol. III, 2nd Ed." (McGraw Hill, New York, 2001).

Peter Siddons, "Crystal Monochromators and Bent Crystals" Ch. 22 of "Handbook of Optics vol. III, 2nd Ed." (McGraw Hill, New York, 2001).

Alan Michette, "Zone and Phase Plates, Bragg-Fresnel Optics" Ch. 23 of "Handbook of Optics vol. III, 2nd Ed." (McGraw Hill, New York, 2001).

Eberhard Spiller, "Multilayers" Ch. 24 of "Handbook of Optics vol. III, 2nd Ed." (McGraw Hill, New York, 2001).

Qun Shen, "Polarizing Crystal Optics" Ch. 25 of "Handbook of Optics vol. III, 2nd Ed." (McGraw Hill, New York, 2001).

Andreas Freund, "Mirrors for Synchrotroin Beamlines" Ch. 26 of "Handbook of Optics vol. III, 2nd Ed." (McGraw Hill, New York, 2001).

F. Cerrina, "The Schwarzschild Objective" Ch. 27 of "Handbook of Optics vol. III, 2nd Ed." (McGraw Hill, New York, 2001).

Marshall K. Joy, "Astronomical X-ray Optics" Ch. 28 of "Handbook of Optics vol. III, 2nd Ed." (McGraw Hill, New York, 2001).

Donald H. Bilderback & Edward D. Franco, "Single Capillaries" Ch. 29 of "Handbook of Optics vol. III, 2nd Ed." (McGraw Hill, New York, 2001).

Carolyn A. MacDonald & Walter M. Gibson, "Polycapillary and Multichannel Plate X-Ray Optics" Ch. 30 of "Handbook of Optics vol. III, 2nd Ed." (McGraw Hill, New York, 2001).

M. Yanagihara et al., "X-Ray Optics", Ch. 3 of "X-ray Spectrometry: Recent Technological Advances", K. Tsuji et al. eds. (John Wiley & Sons, Ltd. Chichester, West Sussex, UK, 2004), pp. 63-131.

A. Erko et al., "X-ray Optics", Ch. 3 of "Handbook of Practical X-Ray Fluorescence Analysis", B. Beckhoff et al., eds. (Springer, Berlin, Germany, 2006), pp. 85-198.

Barry Lai, "X-Ray Microfocusing Optics", Slide Presentation from Argonne National Laboratory, 71 slides, Cheiron Summer School 2007, available at: < http://cheiron2007.spring8.or.jp/pdf/Lai.pdf >.

Sterling W. Cornaby et al., "Design of Single-Bounce Monocapillary X-ray Optics", in Advances in X-ray Analysis: Proceedings of the 55th Annual Conference on Applications of X-ray Analysis, vol. 50 (International Centre for Diffraction Data (Todd), 2007), pp. 194-200.

A. Snigirev & I. Snigireva, "Hard X-Ray Microoptics", Ch. 17 of "Modern Developments in X-Ray and Neutron Optics", A. Erko et al., eds (Springer, Berlin, Germany, 2008), pp. 255-285.

A. Bjeoumikhov & S. Bjeoumikhova, "Capillary Optics for X-Rays", Ch. 18 of "Modern Developments in X-Ray and Neutron Optics", A. Erko et al., eds (Springer, Berlin, Germany, 2008), pp. 287-306.

S. Lagomarsino et al., "Reflective Optical Arrays", Ch. 19 of "Modern Developments in X-Ray and Neutron Optics", A. Erko et al., eds (Springer, Berlin, Germany, 2008), pp. 307-317.

Sterling W. Cornaby, "The Handbook of X-ray Single-Bounce Monocapillary Optics, Including Optical Design and Synchrotron Applications" (PhD Dissertation, Cornell University, Ithaca, NY, May 2008).

Xianghui Zeng et al., "Ellipsoidal and parabolic glass capillaries as condensers for x-ray microscopes", Appl. Opt. vol. 47 (May 2008), pp. 2376-2381.

"Optics and Detectors", Section 4 of X-Ray Data Booklet, 3rd Ed., A.C. Thompson ed. (Lawrence Berkeley Nat'l Lab, Berkeley, CA, 2009). Available at < http://xdb.lbl.gov/ >.

P. Guttmann et al., "Ellipsoidal capillary as condenser for the BESSY full-field x-ray microscope", J. Phys. Conf. Ser. vol. 186 (2009): 012064.

Sterling W. Cornaby et al., "Advances in X-ray Microfocusing with Monocapillary Optics at Chess" Chess News Magazine (2009), pp. 63-66.

T. Matsushita, "Mirrors and Multilayers", Slide Presentation from Photon Factory, Tsukuba, Japan, 65 slides, (Cheiron School 2009,

(56) References Cited

OTHER PUBLICATIONS

SPring-8, Japan, Nov. 2009) available at: < http://cheiron2009.spring8.or.jp/images/PDF/Lecture/Mirror_and_Multilayer_T_Matsushita.pdf >.

X. Zeng et. al., "Glass Monocapillary X-ray Optics and Their Applications in X-Ray Microscopy", in X-ray Optics and Microanalysis: Proceedings of the 20th International Congress, AIP Conf. Proc. vol. 1221, (2010), pp. 41-47.

Roger Falcone et al., "New directions in X-ray microscopy", Contemporary Physics vol. 52, No. 4 (Jul.-Aug. 2010), pp. 293-318.

Carolyn A. MacDonald, "Focusing Polycapillary Optics and Their Applications", X-Ray Optics and Instrumentation vol. 2010, (Oct. 2010): 867049.

Jens Als-Nielsen & Des McMorrow "Refraction and reflection from interfaces", Ch. 3 of "Elements of Modern X-ray Physics, Second Edition", (John Wiley & Sons Ltd, Chichester, West Sussex, UK, 2011), pp. 69-112.

"X-ray Optics for BES Light Source Facilities", Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013). < http://science.energy.gov/~/media/bes/pdf/reports/files/BES_XRay_Optics_rpt.pdf >.

Yoshio Suzuki et al., "Hard X-ray Imaging Microscopy using X-ray Guide Tube as Beam Condenser for Field Illumination" J. Phys: Conf. Ser. vol. 463 (2013): 012028.

* cited by examiner

HIGH BRIGHTNESS X-RAY ABSORPTION SPECTROSCOPY SYSTEM

CROSS-REFERENCE TO RELATED APPLICATIONS

This patent application claims the benefit of U.S. Provisional Patent Application Nos. 62/008,856, filed Jun. 6, 2014; 62/086,132, filed Dec. 1, 2014, and 62/117,062, filed Feb. 17, 2015, all of which are incorporated herein by reference in their entirety.

FIELD OF THE INVENTION

This present invention relates to a high brightness x-ray absorption spectroscopy apparatus for the analysis of chemical/electronic states of element(s) in materials using the x-ray absorption near-edge spectroscopy (XANES) technique, and for the determination of the atomic coordination number and distance of element(s) in materials using extended x-ray fine absorption structure (EXFAS) technique.

BACKGROUND OF THE INVENTION

X-ray absorption spectroscopy is a widely used technique to determine local atomic structure and/or electronic structure of matter. X-ray absorption spectroscopy data are obtained by measuring transmission and/or characteristic fluorescent x-rays of an element in a material as a function of incident x-ray energy over an energy range with sufficiently narrow energy band that corresponds to an absorption edge of an element of interest, at which the incident x-ray photon has sufficient energy to excite core electron(s). The local atomic structure and electronic structure of the material show resonances and exhibit interference effects that affect the x-ray transmission as a function of the incident x-ray energy, so, by measuring the x-ray transmission as a function of x-ray energy, information about the local atomic structure and/or the electronic structure of the material can be determined.

Absorption spectra near x-ray absorption edges are generally divided into the "near edge" region, comprising the first 100 eV near an absorption edge, and the "extended" region, up to 1000 eV higher. Near edge spectroscopy, generally referred to as near edge x-ray absorption fine structure (NEXAFS) spectroscopy, or x-ray absorption near edge spectroscopy (XANES), are the result of transitions of core electrons to low lying unoccupied energy levels, and often has sharp resonance peaks. It is of use in understanding the chemical environment, and in particular the oxidation state of the element involved. Spectroscopy of the more extended energy region, generally referred to as extended x-ray absorption fine structure (EXAFS), exhibits gentle oscillations of absorptivity with energy. These arise from the interactions of the photoelectrons emitted with the surrounding atoms within the structure. From the analysis of EXAFS spectra, distances between atoms can be determined with high precision. The experimental analysis focusing on both spectral regions has been referred to as x-ray absorption fine structure (XAFS).

FIG. 1 illustrates a conventional synchrotron XAFS measurement apparatus, in which a synchrotron x-ray source P80 produces a beam of collimated x-rays P889 (typically collimated using an aperture or pinhole). The x-ray optical system associated with the source P80 may also include beam stops, apertures, or other optical elements to shape the x-ray beam P889 to have particular properties. The collimated x-ray beam P889 then enters a double crystal monochromator P330 comprising a first crystal P330A, which reflects the desired spectral component 889-1 onto a second crystal P330B to further limit the spectral bandwidth to produce a monochromatized x-ray beam 889-2, which is then incident on a sample 240 to be measured. The transmitted x-rays P889-X that pass through the sample 240 are then detected by a detector P290, which will typically transmit its signals to signal processing electronics P292 that then are further processed by an analysis system P295, which often has a display P298 to show data and results to the user. Motion controls for the double crystal monochromator P330 (not shown) are typically provided so that adjustment of the angle relative to the x-ray beam will select a particular narrow range of x-ray energies for transmission through the monochromator P330.

FIG. 2 shows an illustration of XAFS results, in this case for a model iron oxide ($Fe_2O_3$) powder. Data are collected for x-rays with energy near the iron (Fe) K-edge absorption at 7.112 keV. Near edge structure (XANES) is clearly visible, as are the higher energy EXAFS variations from the standard absorption (denoted by $\mu(E)$). From these variations, details of the chemical state and inter-atomic structure of the material may be derived. [Data in FIG. 2 adapted from the PhD dissertation of Mauro Rovezzi, "Study of the local order around magnetic impurities in semiconductors for spintronics." Condensed Matter, Université Joseph-Fourier—Grenoble I, 2009. English. <tel-00442852>.]

Typically, an x-ray beam with an energy bandwidth of less than 1 eV is required for XANES and less than 10 eV for EXAFS measurements. In electron bombardment x-ray sources, the x-ray spectrum typically consists of a continuous spectrum (known as Bremsstrahlung radiation) along with sharp characteristic x-ray fluorescence lines of element(s) in the anode illuminated by the incident electron beam. For XFAS measurement, Bremsstrahlung radiation is typically used. Because intensity oscillations in EXAFS spectra are often less than 10% of the total absorption, and structural parameters can be obtained only after a Fourier transform analysis of the data, highly accurate (0.1% or better) absorption measurements are often required. Therefore, at least a million photon counts are typically required at each energy datapoint.

To meet the narrow energy bandwidth required, a crystal monochromator can be used. Several methods can be used to obtain the required energy bandwidth. One method is to use a pair of flat crystals with appropriate reflection Miller index, such as silicon Si (111), arranged to diffract an incident x-ray beam with a small convergence angle in the dispersion plane (containing the incident and diffraction beam). The required small angular convergence can be obtained for example using a pair of narrow slits separated by a predetermined distance. Sometimes, only one slit is required if the source size in the dispersion plane is small. This method offers several advantages: simple energy scanning by scanning the x-ray beam incidence angle by rotating the monochromator, and a fairly wide energy scanning range using a single crystal, often without need to move the source and the sample in positions and angles, which can be important for many experiments, and results in substantially simpler system and lower cost.

The small convergence angle means that this technique can be widely used for experiments using synchrotron radiation sources, which have high brightness and are highly directional. However, in a laboratory setting, where x-rays are generated in an electron bombardment source, only a small fraction of the x-rays will be collected and used. Consequently, the x-ray flux of a monochromatic x-ray beam obtained using this method from a conventional electron bombardment x-ray source has simply been too low to allow laboratory XAFS measurement.

To circumvent the low x-ray flux and thus low throughput problem, most laboratory source based XAFS systems employ a single bent crystal monochromator in a Rowland circle geometry. In such a system, the x-ray source, the bent crystal, and the slit in front of the sample, are all located on the Rowland circle, with appropriate orientation. Although using a bent crystal can increase the angular acceptance of x-rays generated by the source, Rowland circle based x-ray spectrometers suffer the following drawbacks: difficulty to obtain high x-ray energy resolution due to crystal strain induced by the bending, the requirement of moving at least two of the three major components (source, crystal and slit/sample) for energy scanning. In addition, a single bent crystal covers only a relatively small energy range, so in practice often a set of bent crystals are required. The use of Rowland circle based spectrometers may in part be motivated by the lack of x-ray sources of small size with sufficient brightness, and the lack of x-ray optics for collecting x-rays generated in the source with a large solid angle able to provide an x-ray beam with sufficient angular collimation.

Another performance limiting factor of Rowland circle based monochromator is high order harmonic contamination of the monochromatic x-ray beam because the bent crystal often reflects x-rays of energy equal to an integer multiple of the desired x-ray energy. To circumvent this higher order harmonic contamination problem, low energy electron beam excitation is often used. The use of low energy electrons directly leads to a decrease of x-ray flux because x-ray production efficiency of bremsstrahlung radiation in an electron bombardment x-ray source is approximately proportional to the incident electron energy.

The low performance of conventional laboratory-based x-ray absorption spectroscopy systems has severally limited their utilization. X-ray absorption spectroscopy measurements are currently carried out mostly at synchrotron radiation facilities, which offer high throughput because of their large source brightness and usable x-ray flux over a wide energy range. However, synchrotron radiation sources are large and expensive, often occupying acres of land, and only available in a limited number of locations. As a consequence, access per user group is typically finite and infrequent, particularly for industrial users concerned about protecting intellectual property and/or difficulty justifying important but routine measurements in competition with academic research proposals for lack of pure scientific merit. Other limitations include difficulty in transportation to synchrotron radiation facilities of delicate samples (e.g., fragile or sensitive to oxidization), severe biological and radiological safety considerations, or in-situ experiments requiring special instrumentation that may be unavailable.

XAFS techniques have many applications. In particular, EXAFS can measure local interatomic distances in crystalline and non-crystalline materials. This is a unique capability for non-crystalline materials, such as amorphous solids, solid solutions, dopant and implant materials in semiconductor devices, catalysts, liquids, and organometallic compounds. XANES is particularly useful in determining the oxidation states of the element in its chemical environment. However, these techniques suffer from the lack of a high brightness compact x-ray source that can be used in a laboratory or in the field. There is therefore a need for such a high brightness, compact x-ray system for XAFS measurements.

BRIEF SUMMARY OF THE INVENTION

The present invention discloses an x-ray absorption spectroscopy system comprising a compact x-ray source that provides a high brightness x-ray beam within a finite angular range. This is achieved by using a source configuration that allows linear accumulation of x-rays. The system also comprises an x-ray optical train that collects and collimates the x-ray beam from the high brightness source, a monochromator comprising two flat crystals (henceforth referred to as double crystal monochromator) that monochromatizes the collimated x-ray beam and allows for scanning the x-ray energy, and an x-ray detector that collects x-rays resulting from the interaction of the monochromatic x-ray with matter in a sample for analysis. Optionally, it may also comprise a detector that monitors the intensity of the monochromatic x-ray beam before its incidence on the sample (typically partially transmissive and placed before the sample), and/or a second optical train that focuses the monochromatic x-rays onto the sample.

The linear accumulation x-ray source compromises two or more sub-sources of x-rays, with each sub-source having predetermined x-ray spectral characteristics, and with the sub-sources separated physically from each other by predetermined spatial intervals and aligned with each other along a predetermined axis to allow accumulation of x-rays to increase brightness along that axis within a finite angular range. The x-ray sub-sources are produced by electron bombardment of one or more targets comprising x-ray generating materials. At least one of the targets comprises a substrate of low Z material (the first material) with high thermal conductivity, and also an x-ray generating high Z material (the second material) selected for its x-ray generating properties, such as spectral characteristic and x-ray production efficiency, having at least one dimension less than 10 micrometers. In some embodiments, the linear accumulation x-ray source is a line source to increase throughput. In some preferred embodiments, the x-ray source position is scanned to increase data collection throughput.

As part of the system, an x-ray optical train is configured to collect and collimate or focus the x-rays from the high brightness source to produce a high flux collimated x-ray beam over an energy range of interest. The x-ray optical train will typically comprise at least one axially symmetric x-ray mirror optic with a reflecting surface profile selected from paraboloids and/or from type I Wolter optics, which is comprised of an ellipsoid and a hyperboloid. The reflecting surface is typically glass, either uncoated or coated with high mass density material or a multilayer coating. The reflecting surface material should not contain elements with absorption edges in the x-ray energy range of interest. The optical train may additionally include at least one pair of slits or pinholes/apertures to collimate the angular convergence of the x-ray beam in one direction for some embodiments.

A double crystal monochromator monochromatizes the collimated high flux x-ray beam without changing the x-ray beam propagation direction using a none-dispersive configuration, i.e. two identical crystals arranged in parallel. The crystal diffraction Miller index is selected to obtain the energy resolution required. For XANES measurement, the energy range to be scanned is typically within 50-100 eV of the absorption edge of the element of interest with an x-ray energy bandwidth less than 1 eV. For EXAFS, an energy scan of 500-1000 eV is typical, with an x-ray energy bandwidth less than 10 eV. The double crystal monochromator will typically comprise a rotary stage with rotation axis that is parallel to the crystal diffraction plane and perpendicular to the x-ray beam propagation direction.

At least one detector receives x-rays from the sample in response to the interaction of the incident x-ray beam with the sample, and produces signals indicative of properties of the sample. The x-ray signals from the sample might include x-ray transmission through the sample, and/or x-ray fluorescence of an element of interest as a function of the x-ray energy of the incident x-ray beam. In some embodiments, an additional optical train and/or monochromator may be placed before the detector to remove background x-rays and improve signal to noise.

An electromechanical system will also typically be present to control the source, the components of the optical train, the monochromator, the positioning the sample with respect to the incident x-ray beam, and the detector. This system for electromechanical control may be linked to a data analysis system that acquires data corresponding to the x-ray signals, and performs calculations that determine the desired properties of the sample.

Note: The accompanying drawings, which are incorporated in and constitute a part of the specification, illustrate exemplary embodiments, features, and aspects of the invention and, together with the description, serve to explain the principles of the invention. The drawings are not necessarily to scale; emphasis has instead been placed upon illustrating the principles of the invention.

DETAILED DESCRIPTIONS OF EMBODIMENTS OF THE INVENTION

X-Ray Absorption Spectroscopy System

Figure 1:
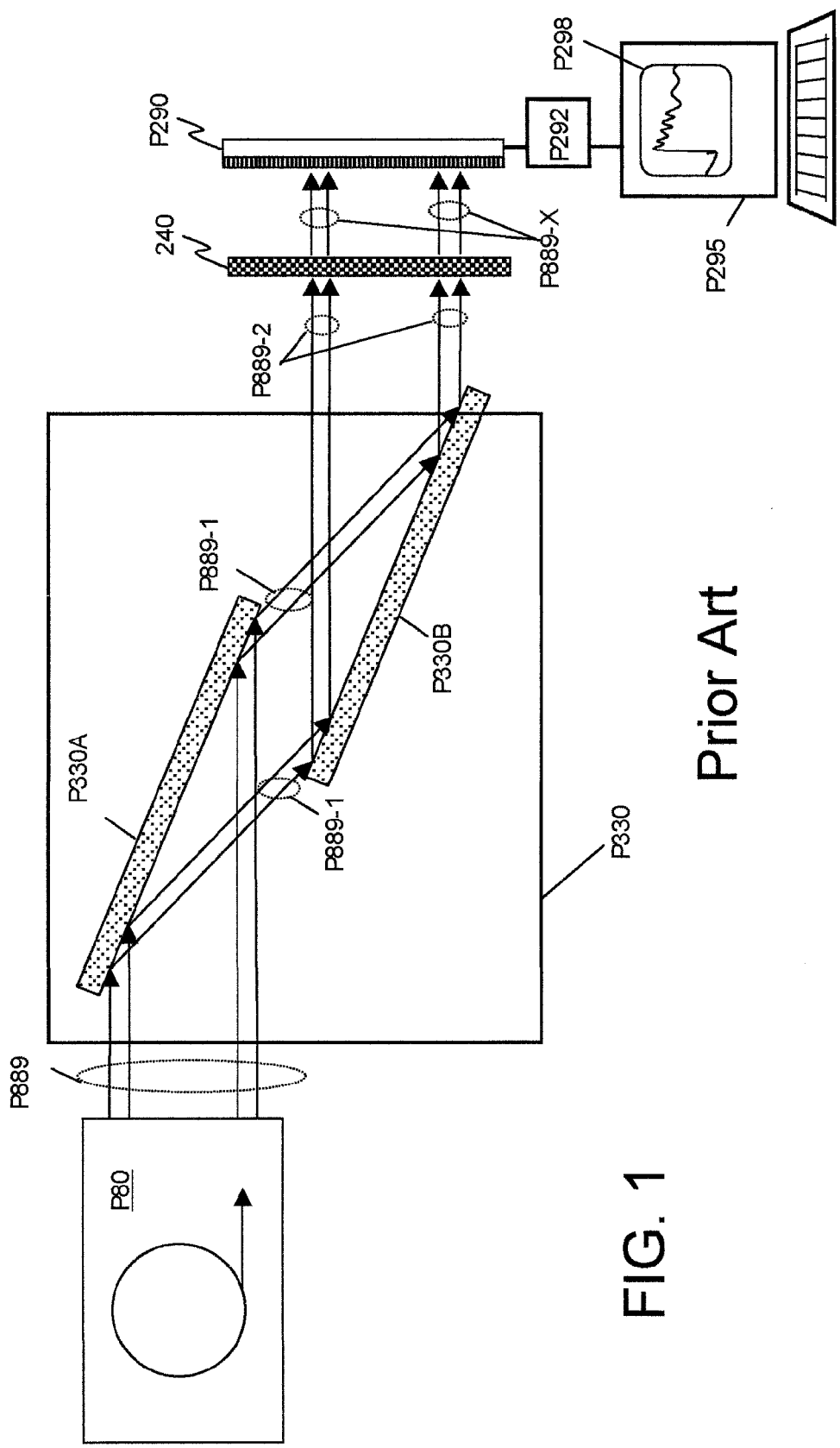
FIG. 1 presents a schematic view of a prior art x-ray absorption fine structure (XAFS) measurement system.
Figure 2:
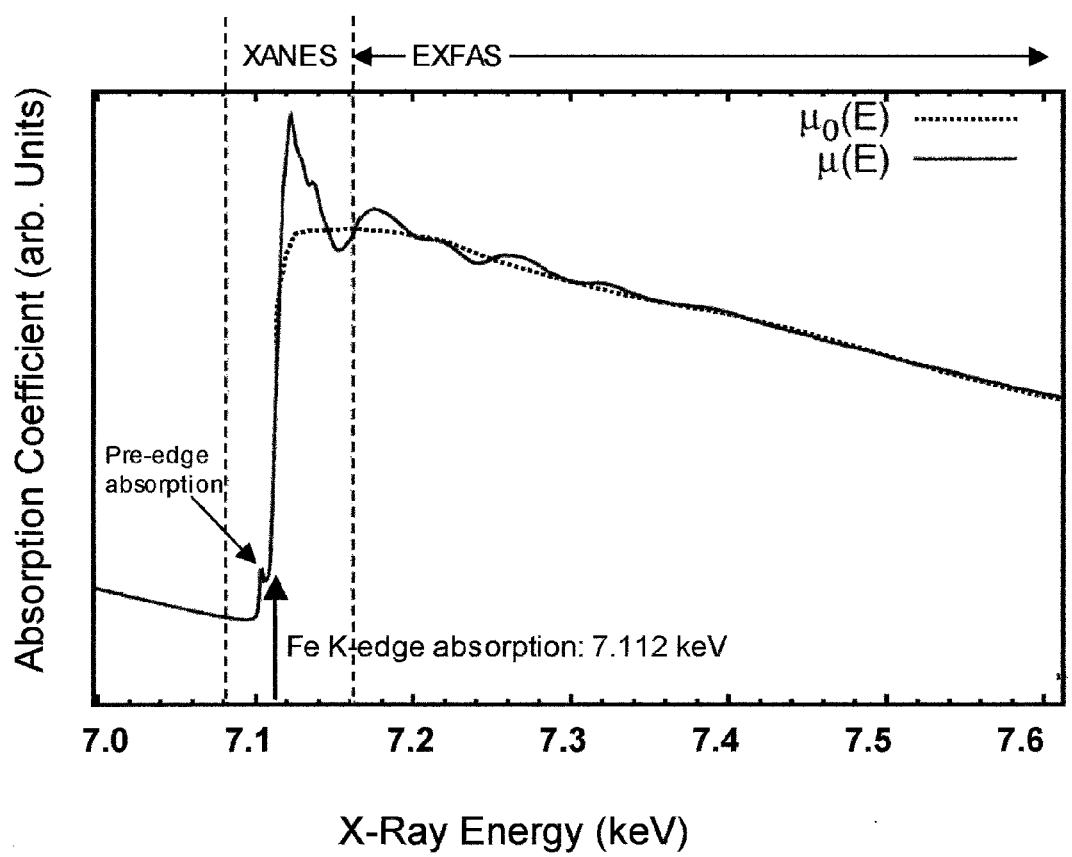
FIG. 2 illustrates a prior art plot of a representative x-ray absorption fine structure (XAFS) spectrum for an iron oxide powder.
Figure 3:
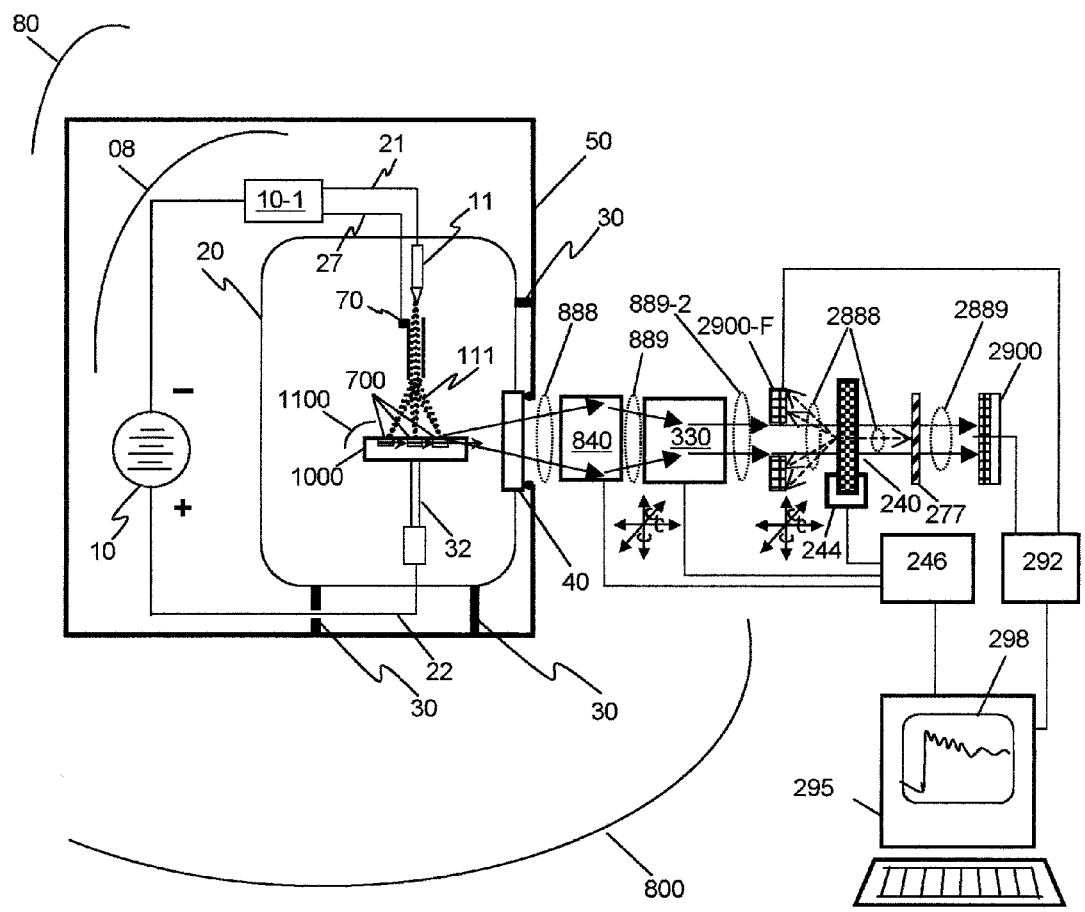
FIG. 3 schematically illustrates an XFAS system according to the invention.

FIG. 3 schematically illustrates an embodiment of the present invention for an x-ray absorption spectroscopy system.

The x-ray generator 08 comprises a vacuum environment (typically $10^{-6}$ torr or better) commonly maintained by a sealed vacuum chamber 20 or using active pumping, and manufactured with sealed electrical leads 21 and 22 that pass from the negative and positive terminals of a high voltage source 10 outside the vacuum chamber 20 to the various elements inside the vacuum chamber 20. The x-ray source 80 will typically comprise mounts 30 which secure elements of the x-ray generator 08 such as the vacuum chamber 20 to a housing 50, and the housing 50 may additionally comprise shielding material, such as lead, to prevent x-rays from being radiated by the source apparatus 80 in unwanted directions. Inside the vacuum chamber 20, an emitter 11 connected through the lead 21 to the negative terminal of a high voltage source 10, which serves as a cathode and generates a beam of electrons 111, often by running a current through a filament. Any number of prior art techniques for electron beam generation may be used for the embodiments of the invention disclosed herein.

A target 1100 comprising a target substrate 1000 and regions of x-ray generating material (shown in FIG. 3 as a set of embedded microstructures 700) is electrically connected to the opposite high voltage lead 22 and target support 32 to be at ground or positive voltage relative to the electron emitter 11, thus serving as an anode. The electrons 111 accelerate towards the target 1100 and collide with it at high energy, with the energy of the electrons determined by the magnitude of the accelerating voltage. The collision of the electrons 111 into the target 1100 induces several effects, including the generation of x-rays 888, some of which exit the vacuum chamber 20 and are transmitted through a window 40 that is transparent to x-rays.

The target 1100, as will be further described below, is configured to have multiple sub-sources of x-rays generated from points that are generally aligned with each other such that they produce x-rays that may have linear accumulation, leading to higher brightness. Microstructured targets such as those that may be used in embodiments of the invention disclosed herein have been described in detail in the co-pending US Patent Application entitled STRUCTURED TARGETS FOR X-RAY GENERATION (U.S. patent application Ser. No. 14/465,816, filed Aug. 21, 2014), which, along with the provisional Applications incorporated therein and to which it claims benefit (Application Nos. 61/873,735, filed on Sep. 4, 2013, 61/880,151, filed on Sep. 19, 2013, 61/894,073, filed on Oct. 22, 2013, and 61/931,519, filed on Jan. 24, 2014), is hereby incorporated by reference in its entirety. Furthermore, sources using these targets that have a linear accumulation of x-ray sources as are described more fully in the co-pending U.S. Patent Application entitled X-RAY SOURCES USING LINEAR ACCUMULATION by the inventors of the present invention (U.S. patent application Ser. No. 14/490,672 filed Sep. 19, 2014), which, along with the provisional Applications incorporated therein and to which it claims benefit (Application Nos. 61/880,151, filed on Sep. 19, 2013, 61/894,073, filed on Oct. 22, 2013, 61/931,519, filed on Jan. 24, 2014, and 62/008,856, filed on Jun. 6, 2014), is also hereby incorporated by reference in its entirety. Any of the target and source designs and configurations disclosed in the above referenced co-pending Applications may be considered as alternative components and designs in any or all of the embodiments of the x-ray absorption spectroscopy systems according to the invention disclosed herein.

In some embodiments of the invention, there may also be an electron control mechanism 70 such as an electrostatic lens system or other system of electron optics that is controlled and coordinated with the electron dose and voltage provided by the emitter 11 by a controller 10-1 through a lead 27. The electron beam 111 may therefore be scanned, focused, de-focused, or otherwise directed onto a target 1100 comprising one or more microstructures 700 fabricated to be in close thermal contact with the substrate 1000. In addition to providing one or more electron beam(s) with predetermined properties (e.g. electron energy, current, and focal spot size), such a control mechanism 70 may also direct the respective electron beams to its desired position on one or more x-ray target(s) to generate x-rays at the positions of sub-sources along a predetermined direction.

The system will typically comprise an optical train 840 to collect the x-rays from the source and create an x-ray beam 889 with predetermined angular properties. The system will typically also comprise a monochromator 330 to take the x-ray beam 889 and select certain wavelengths to form a monochromatic beam 889-2 and direct it towards the sample 240 to be investigated. The combined x-ray source apparatus 80, optical train 840 and monochromator 330 may be considered together as an x-ray illuminator 800. In some embodiments, the monochromator 330 may be optionally followed with an additional optical train that focuses the x-ray beam upon the sample.

The sample 240 is typically held in a mount 244, which may have motion controls for x-y- and z translation, as well as rotation about these axes as well. These motion controls may be managed by a controller 246, which may also have input into the x-y-z and rotation controls of the optical train 840 and/or the monochromator 330. The data collection system may comprise an x-ray detector or spectrometer 2900 to collect the transmitted x-rays 2889. The system may also comprise an additional x-ray filter 277 or other component with predetermined spectral properties that may pass the transmitted x-rays 2889 while blocking any x-ray fluorescence 2888 that may be generated in the sample 240. The system may also comprise an additional x-ray detector or spectrometer 2900-F to collect fluorescence x-rays 2888.

The fluorescence detector may be of any type that is energy-resolving, including wavelength dispersive spectrometer types, energy dispersive detectors, or microcalorimeters. Shown in the figure is an energy dispersive type detector with a pinhole, such as a silicon drift detector with a through-hole for the incident beam. Such a configuration allows a large solid angle of collection. However, other embodiments may be envisioned in which a fluorescence-type detector without a through-hole is offset at an angle relative to the sample, either before or after the sample. Depending on the measurement technique being employed, the detector 2900 and/or spectrometer 2900-F may comprise x-ray optical elements and sensors designed to discriminate between x-ray energies.

For XAFS measurement, x-ray absorbance as a function of x-ray energy is obtained by scanning the x-ray energy over a predetermined energy range. The x-ray absorbance is obtained by normalizing the intensity of the x-ray beam passing through the sample 240 to the incident x-ray beam 888 intensity. In some embodiments, an additional detector may be used to directly measure the intensity of the incident x-ray beam 888. This incident intensity detector may be an independent, partially transmissive detector placed in after the monochromator 330 or front of the sample 240, or may be incorporated as part of the monochromator 330 as well. Alternatively, the incident x-ray beam 888 intensity as a function of x-ray energy may also be determined using the detector 2900 by removing the sample from the x-ray beam path. In some embodiments, an x-ray spectrometer 2900-F may record x-ray fluorescence signals, and is used together with or instead of the x-ray detector 2900. The x-ray absorption spectroscopy apparatus may additionally comprise slit(s) to eliminate or reduce unwanted x-rays (such as x-rays scattered outside the collimated x-ray beam) to reach the sample.

For XAFS measurement, the x-ray flux F of the monochromatic x-ray beam incident on the sample using an embodiment of the present invention illustrated in FIG. 3 is given by:

$$F = \eta B_s S_1 S_2 \Delta\theta_1 \Delta\theta_2 \Delta E/E \quad \text{[Eqn. 1]}$$

where $B_s$ is the x-ray beam brightness at the sample (defined as number of x-rays per unit area and per unit solid angle illuminating the sample and per 0.1% relative spectral bandwidth), $\eta$ is the optical system efficiency for relaying x-rays from the source to the sample, $S_1$ is the source size in the energy dispersion plane (the plane containing the incident and diffracted x-ray beam of the double crystal monochromator) and $S_2$ is the source size in the out-plane that is perpendicular to the dispersion plane and the x-ray beam axis, $\Delta\theta_1$ and $\Delta\theta_2$ are the x-ray beam angular divergence angle in the scattering direction and the out-plane directions, respectively, and $\Delta E/E$ is the relative spectral bandwidth required for a measurement.

The x-ray beam brightness $B_s$ at the sample is typically smaller than the x-ray source brightness (B) because the inherent low focusing efficiency and aberrations of the x-ray optical train lead to blurring and therefore an increase in the effective x-ray source size. $B_s$ and B are approximately related by:

$$B_s = B \frac{S_1 S_2}{S_1 S_2 + \delta^2} \quad \text{[Eqn. 2]}$$

where $\delta$ is the full width half maximum (FWHM) of the point spread function of the x-ray optical train, assuming that the optical property of the optical train between the source and the sample is axially symmetric and the optical train is configured to collimate x-rays from the source.

The x-ray energy bandwidth $\Delta E$ passing through a double crystal monochromator is approximately given by $$\Delta E = E \cot(\theta) \Delta\theta_1 \quad \text{[Eqn. 3]}$$

where E is the x-ray energy of the monochromatic x-ray beam after the double crystal monochromator, and $\cot(\theta)$ the cotangent of the Bragg angle (the angle between the incident x-ray beam and the crystal Bragg plane).

Various embodiments of the present invention are designed to obtain a large flux F with a bright linear accumulation x-ray source, a high performance x-ray optical train comprising an x-ray mirror optic with a small point spread function and a large solid angle of collection of x-rays generated by the source, a double crystal monochromator providing a large value of the product of its diffraction efficiency and $\cot(\theta)\Delta\theta_1$, while achieving a desired energy bandwidth $\Delta E$.

X-Ray Source.

Various embodiments of the linear accumulation x-ray source comprise a plurality of x-ray sub-sources, and may comprise at least one target comprising a substrate (the first material) of low Z material with high thermal conductivity, such as diamond or beryllium, and an x-ray generating material (the second material), such as copper, molybdenum, or tungsten, selected for x-ray generating property, such as spectral characteristic and x-ray production efficiency, and having at least one dimension less than 10 micrometers. In some embodiments, the thermal conductivity of the targets is mainly determined by the thermal conductivity of the substrate material, which allows the use of x-ray generating materials with lower thermal conductivity otherwise not suitable as x-ray target materials in a contiguous single material target employed in prior art, such as germanium and lead, consequently allowing more options for materials to be used to produce characteristic x-ray lines.

Figure 4:
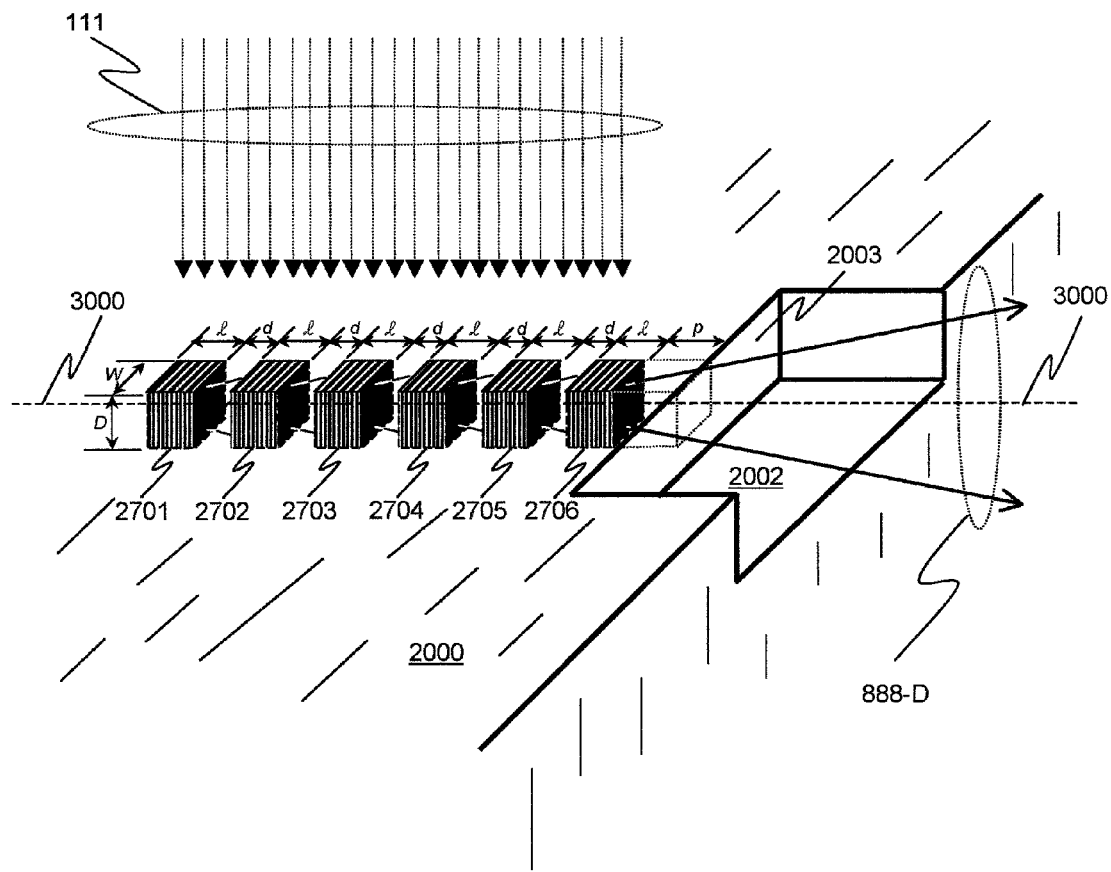
FIG. 4 schematically illustrates a linear accumulation x-ray target comprising sub-sources as used in some embodiments of the invention.

FIG. 4 schematically illustrates an embodiment of a portion of a linear accumulation x-ray source as may be used in some embodiments of the present invention that provides high x-ray brightness. In this source, six discrete microstructures 2701, 2702, 2703, 2704, 2705, 2706 comprising x-ray generating materials selected for x-ray generating properties are embedded or buried in a substrate 2000 and configured at or near a recessed edge 2003 of the substrate 2000 by a shelf 2002, where the material of the substrate is of low average atomic number, high thermal conductivity and high melting point. The x-ray generating microstructures 2701, 2702, 2703, 2704, 2705, 2706 are arranged in a linear array along a predetermined axis 3000, and radiate x-rays 888-D when bombarded with electrons 111. Along the direction within a divergence angle $\psi$ of the axis 3000, x-rays generated in the six sub-sources accumulate and appear to be generated from a single sub-source. The angle range is approximately limited to smaller value of D and W divided by the total length of the x-ray generating region 6*(l+d).

The thickness of the bar D (along the surface normal of the target) is selected to be between one-third and two-thirds of the depth of the incident electron penetrating into the substrate for optimal thermal performance, but it can be bigger or smaller. The chosen value determines the source size along that direction. Its selection also depends on the accelerating voltage, since the penetration of the electron beam increases with energy. The width of the bar W is selected to obtain a desired source size in the corresponding direction. Though W≈1.5 D is illustrated in FIG. 4, it could also be substantially smaller or larger, depending on the size of the source spot desired.

In FIG. 4, each of the discrete microstructures 2701, 2702, 2703, 2704, 2705, 2706 are shown to have equal length l along the axis 3000. The total length of all the six discrete microstructures, 6 l will commonly be set to be ~2 L, where L is the x-ray linear attenuation length of the materials of the discrete microstructures for the x-ray energy of interest, but a value of 0.5 L to 4 L may be selected. The thickness of the substrate material between two adjacent discrete microstructures is preferably of a value between 0.5 l to 3 l, optimized by considering the relative thermal conductivity and mass density of the materials of the substrate and the discrete microstructures, the x-ray linear attenuation length of the substrate at the x-ray energy of interest, and the desired divergence angle V.

In one embodiment of the linear accumulation source of the present invention, the incident electron beam uniformly illuminates the area of the substrate containing the discrete microstructures. In this case, because the electron energy deposition rate in a material is proportional to the mass density, the ratio of the energy deposited in the substrate between two adjacent discrete microstructures and in the discrete microstructures is approximately equal to the ratio of their mass densities. Another preferred embodiment of the invention is that the incident electron beam is spatially modulated so that a large fraction of it is incident on the discrete microstructures. This makes efficient use of the incident electron energy for x-ray production and reduces the electron energy deposition in the substrate and improves thermal dissipation of the discrete microstructures.

Each of the discrete microstructures has five faces transferring heat into the substrate, increasing the heat transfer away from the discrete microstructures 2701-2706 and into the substrate. As illustrated, five of six faces of the microstructure are in close thermal contact with the substrate, but adequate heat transfer is expected to occur if half or more of the surface area of the microstructure is in close thermal contact with the substrate. As illustrated, the separation between the sub-bars is a distance d≈l, although larger or smaller dimensions may also be used, as discussed above.

The distance between the edge of the shelf and the edge of the x-ray generating material p as illustrated is p≈W, but may be selected to be any value, from flush with the edge 2003 (p=0) to as much as 5 mm, depending on the x-ray reabsorption properties of the substrate material for the x-ray energy of interest, the relative thermal properties of the materials of the substrate and the discrete microstructures, and the amount of heat expected to be generated when bombarded with electrons. For example, in some embodiments, it may be generally preferred that the x-ray transmission through the distance p is greater than 50%. X-rays that are generated are collected from the side of the anode, most preferably at near-zero take-off angles (defined as the angle between the x-ray beam axis and the anode surface).

Although the discrete microstructures shown in FIG. 4 are in the shape of rectangular bar and have equal size, other any number of shapes and sizes can be used to achieve high x-ray source brightness using the linear accumulation design principle from plural of sub-sources and the use of the discrete microstructures embedded or buried in a substrate to improve the thermal dissipation property of the x-ray generating material of each sub-source, such as cubes, rectangular blocks, regular prisms, right rectangular prisms, trapezoidal prisms, spheres, ovoids, barrel shaped objects, cylinders, triangular prisms, pyramids, tetrahedra, or other particularly designed shapes, including those with surface textures or structures that enhance surface area, to best generate x-rays of high brightness and that also efficiently disperse heat. Furthermore, the x-ray generating material in each of the sub-sources may not be of single uniform material but comprise additional finer structures of x-ray generating material.

Figure 5:
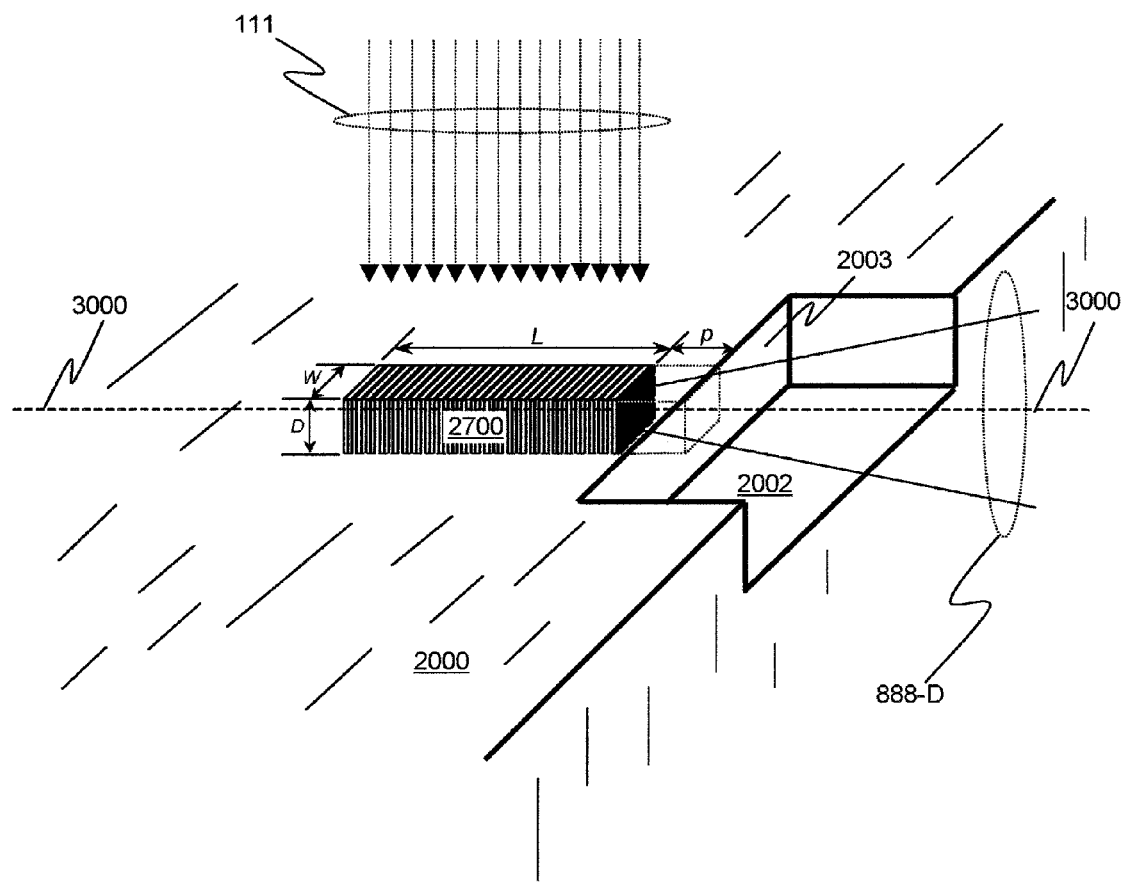
FIG. 5 schematically illustrates a linear accumulation x-ray target comprising a monolithic x-ray generating region as used in some embodiments of the invention.

FIG. 5 schematically illustrates an embodiment of the present invention to generate x-rays 888-D comprising a single microstructure 2700 instead of the discrete microstructures of FIG. 4. In this illustration, the width W and depth D into the substrate of the microstructure 2700 are the same as in FIG. 4, while the accumulated length L of the microstructure 2700 is equal to 6 l. In other words, the volume of x-ray generating material in FIGS. 4 and 5 is the same, and a similar volume of x-rays may be produced by similar excitation by an electron beam 111. Similar design considerations on D, W, L, and p for FIG. 4 apply here.

Figure 6:
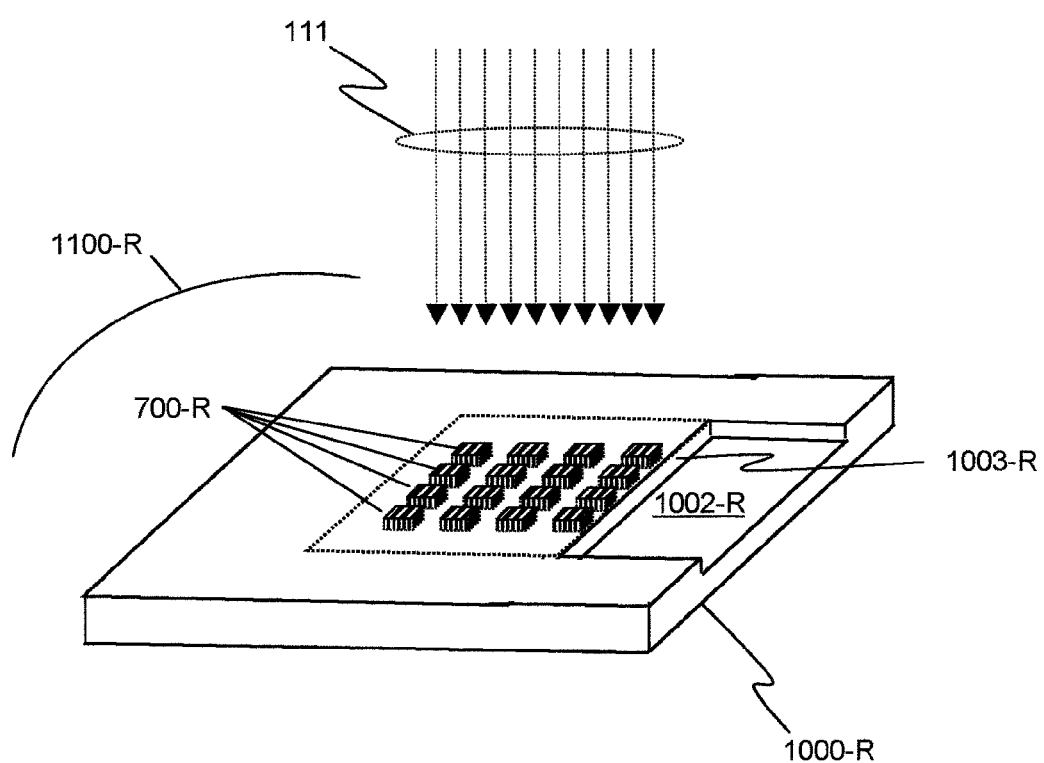
FIG. 6 schematically illustrates a linear accumulation x-ray target as used in some embodiments of the invention in which multiple sub-sources are embedded in a substrate with a recessed shelf.

In FIG. 6, a variation of the source target 1100-R as used in some embodiments of the invention is shown, comprising a two-dimensional array of microstructures 700-R embedded in a substrate 1000-R. This functions on a similar principle to the one-dimensional array of microstructures shown in FIG. 4. Each of the microstructures 700-R acts as a sub-source of x-rays when bombarded by an electron beam 111. The microstructures 700-R as shown are arranged near the edge 1003-R of a recessed shelf 1002-R formed in the substrate 1000-R. The combination of the high thermal conductivity of the substrate and the small dimension of the discrete microstructures allows heat to be efficiently drawn out of the x-ray generating material, and in turn allows bombardment of the discrete microstructures with higher electron density and/or higher energy electrons, leading to greater x-ray brightness and flux, especially along take-off angles near zero degrees.

It should also be noted here that, when the phrase "discrete microstructure" is used herein, it is specifically referring to microstructures comprising x-ray generating material, preferably with at least one dimension smaller than 100 µm. Likewise, it should be noted that, although the phrase "discrete microstructure" is used, x-ray generating structures with at least one dimension smaller than 1 micron, or even as small as nano-scale dimensions (i.e. greater than 10 nm) may also be described by the phrase "discrete microstructures" as used herein as long as the properties are consistent with the geometric factors for sub-source size and pitches set forth in the various embodiments.

It should also be noted that here that, when the word "sub-source" is used it may refer to a single discrete microstructure of x-ray generating material, or an ensemble of smaller microstructures of x-ray generating materials, illuminated by a single electron beam.

The x-ray generating material used in the target should have good thermal properties, such as a high melting point and high thermal conductivity, in order to allow higher electron power loading on the source to increase x-ray production. The x-ray generating material should additionally be selected for good x-ray production properties, which includes x-ray production efficiency (proportional to its atomic number) and in some cases, it may be desirable to produce a specific spectra of interest, such as a characteristic x-ray spectral line. For example, targets are often fabricated using tungsten, with an atomic number Z=74, due to its efficient x-ray production and its high thermal conductivity.

Figure 7:
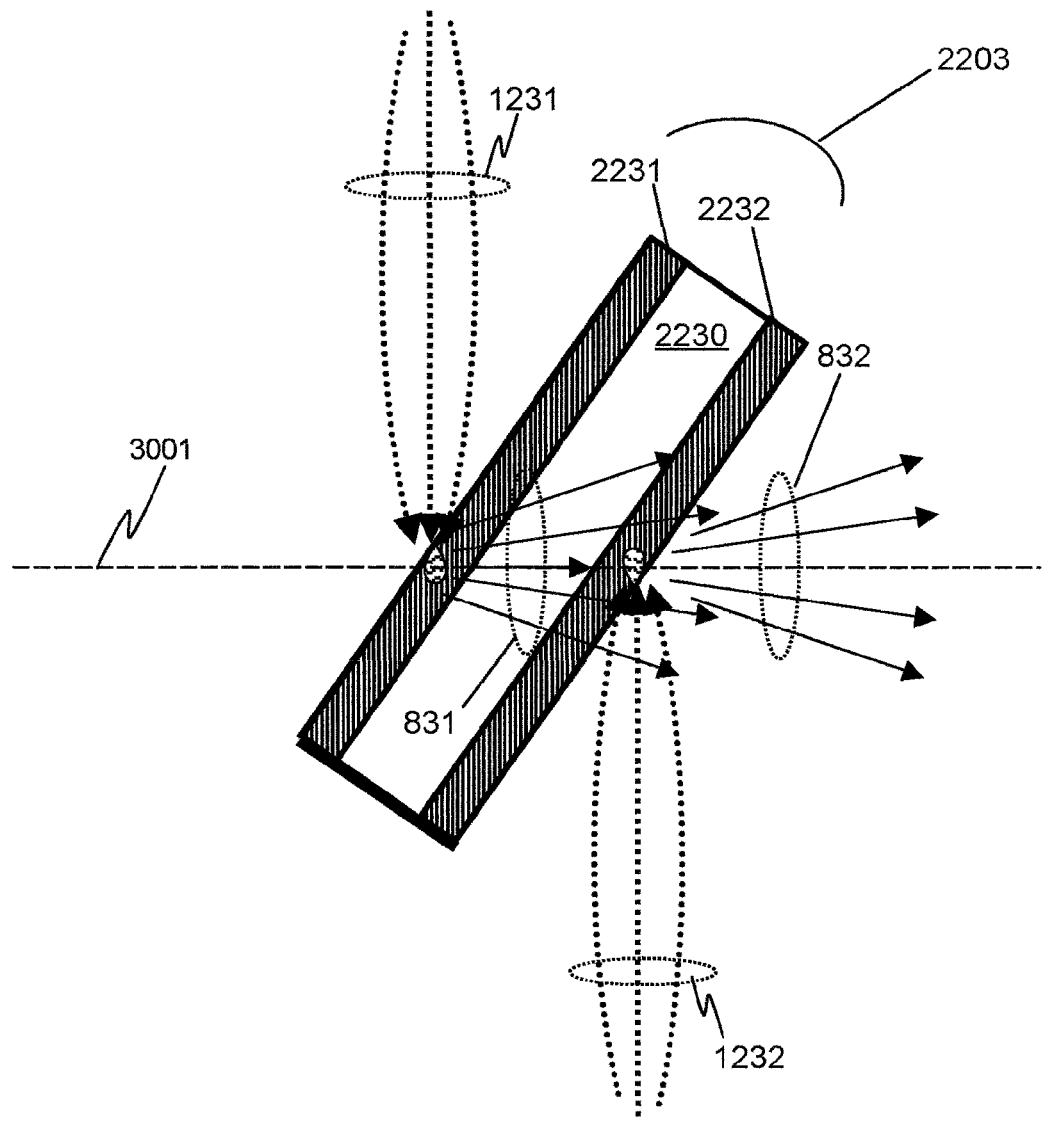
FIG. 7 schematically illustrates a cross section of a two-sided linear accumulation x-ray source as used in some embodiments of the invention.

FIG. 7 schematically illustrates an embodiment of the linear accumulation x-ray source employed in various x-ray source embodiments of the present invention that comprises two sub-sources sharing a common substrate 2230. The substrate may be a first material of low atomic number, low mass density, high thermal conductivity and high melting point, aligned to increase linear accumulation of x-rays along an axis 3001 connecting the two sub-sources. In this embodiment, the source will have two electron beams 1231 and 1232 that are controlled to bombard the respective x-ray generating materials 2231 and 2232 coated on the common substrate 2230 and generate x-rays 831 and 832, respectively.

The x-ray generating materials are sufficiently thick for efficient generation of x-rays of desired spectra but sufficiently thin for high transmission of the desired x-rays. The underlying principle is that the electron penetration depth is typically much smaller than the x-ray linear attenuation length, especially for higher energy x-rays. The thickness of the x-ray generating materials 2231 and 2232 is typically selected to be less than or comparable to the depth of the incident electron beam penetrating into the x-ray generating materials 2231 and 2232, a larger value may be used. If the bombardment occurs at an angle to the surface normal, as illustrated, the angle of incidence can also affect the selection of the coating thickness. Although the tilt of the target 2203 relative to the electron beams 1231 and 1232 is shown as ~45°, any angle from 0° to 90° that allows x-rays to be generated may be used.

The material of the common substrate 2230 is typically selected from a material of low Z material with high thermal conductivity, such as diamond, diamond like material, and beryllium, and silicon carbide. The thickness of the common substrate is selected to have high x-ray transmission for the x-ray energy of interest, often greater than 50%. The distance between the two sub-sources is generally greater than the incident electron beam size.

It is possible that one or more of the anodes of the sub-sources has a very thin substrate or even zero thickness in the impact region of the electron beam(s). It is typical that the anodes (with or without the substrate) of the sub-sources are supported on a support frame with an opening reasonably larger than the incident electron beam or x-ray source size. The support frame will typically have high thermal conductivity and may be cooled using techniques well known to those skilled in the art. In some embodiments, the frame will be cooled to a temperature of minus 90 centigrade when the substrate or the frame is made of diamond to make use of the increased thermal conductivity of diamond with decreasing temperature.

Figure 8:
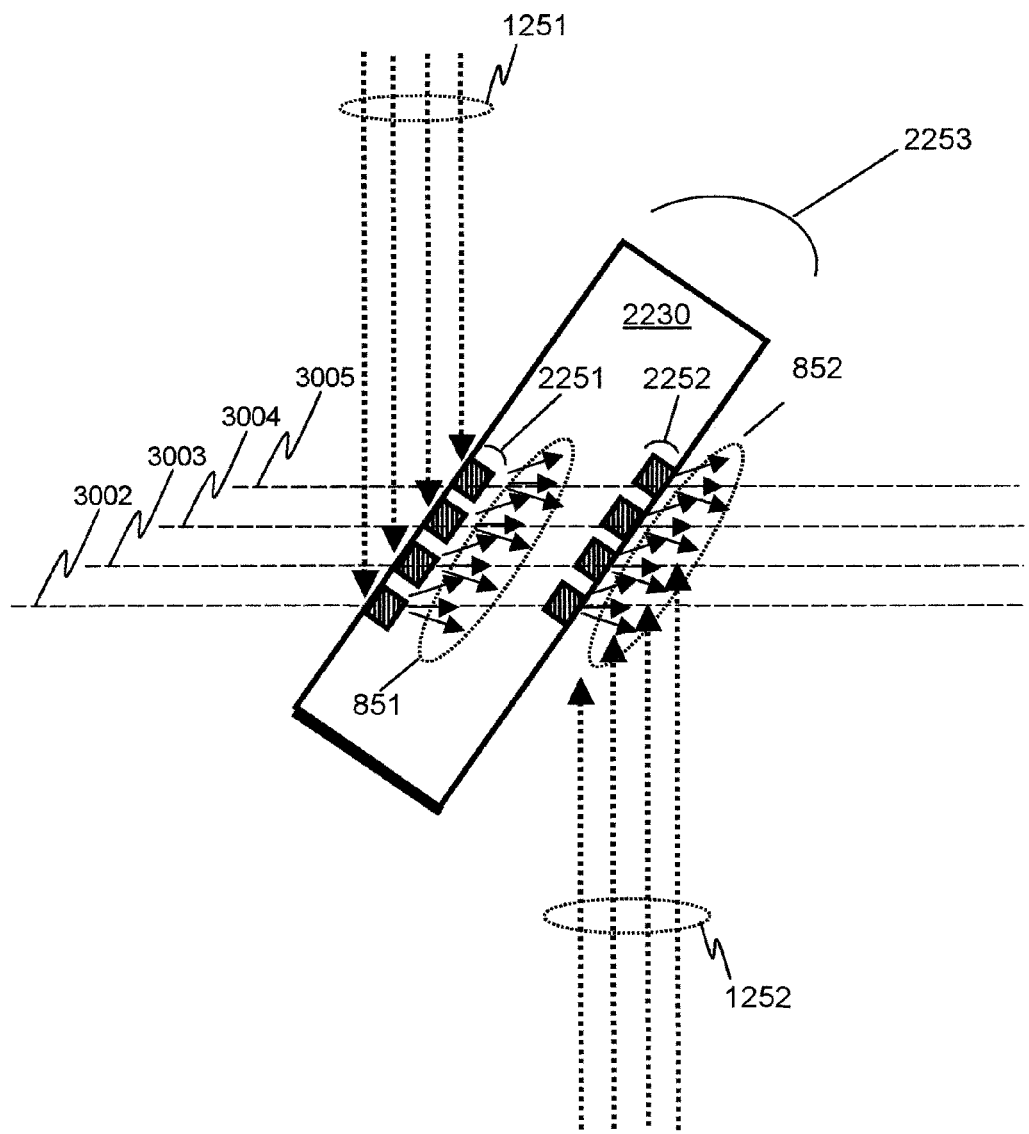
FIG. 8 schematically illustrates a cross section of a two-sided linear accumulation x-ray source as used in some embodiments of the invention.

Though the x-ray generating materials 2231 and 2232 in FIG. 7 are shown as extended target structures comprising a layer of single material, in other embodiments at least one of the single material layer target structures may be replaced with a region comprising a plurality of discrete microstructures of x-ray generating materials embedded or buried in the common substrate 2230, such as those illustrated in the tar 2253 of FIG. 8. In this figure, each of the discrete microstructures in the sets of microstructures 2151 and 2152 acts as an x-ray sub-source, generating x-rays 851 and 852, respectively, when illuminated by electron beam 1251 and 1252, respectively. When aligned with each other along axes 3002-3005, these also produce a higher brightness x-ray beam with an extended beam profile that operates on the same principle the source as illustrated in FIG. 7.

Figure 9:
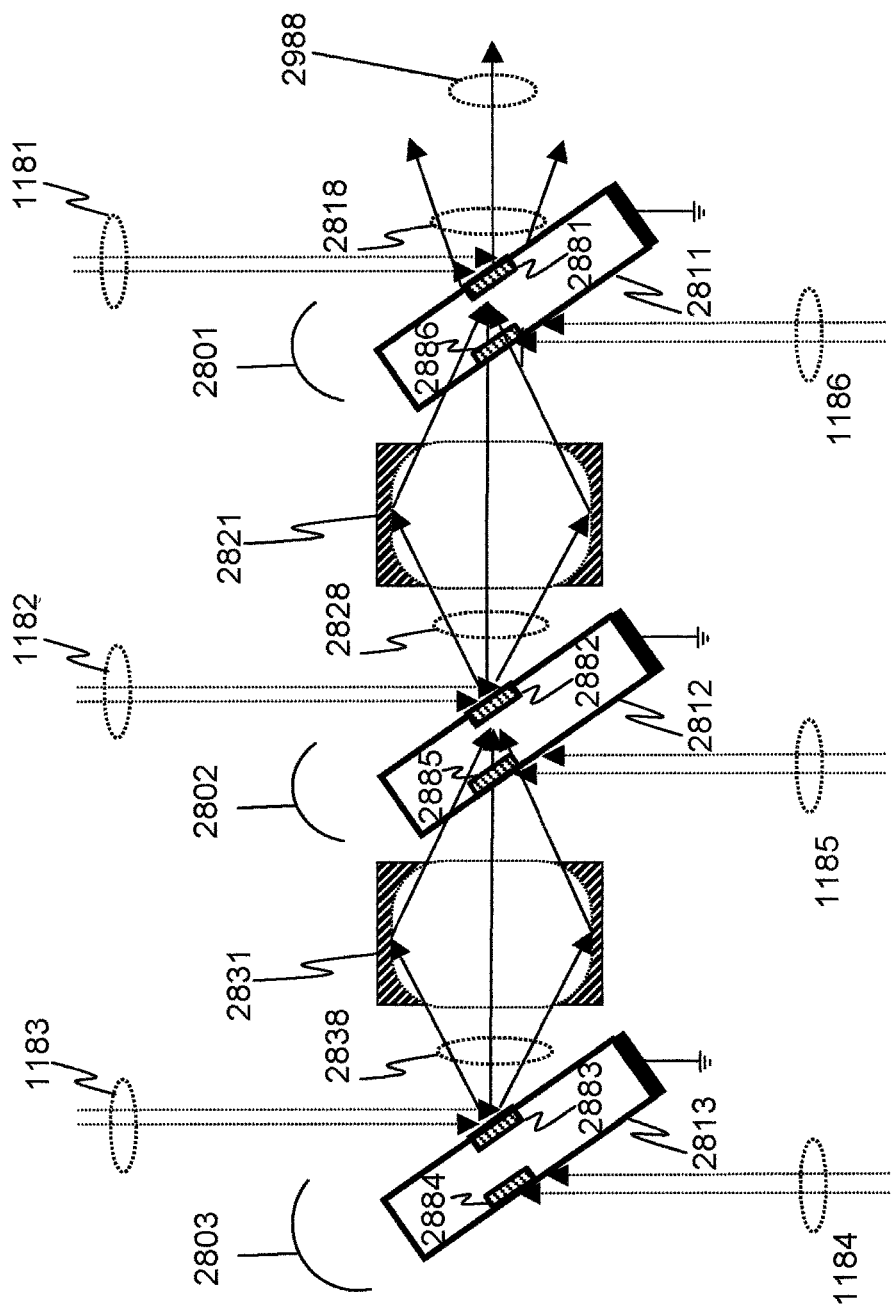
FIG. 9 schematically illustrates a linear accumulation x-ray source comprising optics between sub-sources as used in some embodiments of the invention.

FIG. 9 schematically illustrates yet another embodiment of a linear accumulation x-ray source employed in various embodiments of the present invention that comprises a plurality of targets 2801, 2802, and 2803 with x-ray generating material fabricated on both sides of the respective substrates and aligned along a predetermined axis. Each target radiates x-rays 2818, 1828, 2838 when bombarded with electrons. Imaging optics (2821 or 2831) collect and image x-rays from one sub-source, for example, 2883, to another sub-source, for example, 2882, on a different substrate so that x-rays from the two sub-sources appear to originate from a single sub-source at 2882 when viewed along the axis. Aligning multiple sources of x-ray generation in this manner can achieve an output x-ray beam 2988 having linear accumulation of x-rays and higher brightness. As shown, each of the sub-sources has an electron beam (1181, 1182, 1183, 1184, 1185, and 1186) corresponding to a target structure containing an x-ray generating material (2881, 2882, 2883, 2884, 2885, 2886, respectively). The x-ray target structure may be a layer of the x-ray generating material deposited on its respective substrate, as was illustrated in FIG. 7, or comprise a plurality of the discrete microstructures fabricated in close thermal contact with (such as embedded in or buried in) with its respective substrate, as is illustrated in FIG. 8.

To preserve the brightness of the sub-sources, the x-ray imaging optic that collects the generated x-rays may have a point spread function less than the effective source size of the two sub-sources, the smaller one if two sub-sources have different source sizes. The focusing efficiency of the x-ray imaging optics 2831 and/or 2832 may be designed to be greater than 50%. The surface profiles of these x-ray mirrors that collect the x-rays generated by one sub-source and relay them to the next sub-source may be designed such that the x-rays with the desired x-ray energy incident on the x-ray mirror surface at a grazing angle smaller than or equal to the critical angle for total reflection of the mirror surface material at the desired x-ray energy. The mirror surface material may be glass, or coated either with a high mass density material to increase the critical angle for total reflection to collect more x-rays from the linear accumulation x-ray source. It is important that the material of the reflecting surface doesn't contain elements with x-ray absorption edges in the x-ray spectra of interest for a given measurement. Typical mirrors that collect and focus x-rays may surfaces corresponding to ellipsoids, although other surface configurations or optical designs that collect and focus x-rays, such as those using combinations of Wolter optics or those using polycapillary optics, will be known to those skilled in the art.

FIG. 9 shows six x-ray sub-sources with target structures fabricated on three separate substrates with every two sub-sources sharing a common substrate, and each illuminated by a corresponding electron beam, but any number of regions of x-ray generating material can be aligned in this manner to produce a high brightness x-ray source with linear accumulation. This linear accumulation method can be repeated multiple times to obtain higher source brightness along the axis of alignment. The x-ray targets including the substrate and x-ray generating materials in at least one direction along the axis are selected to have high x-ray transmission, preferably greater than 50%, for the x-ray energy of interest.

It is possible that one or more of the anodes of the sub-sources has a very thin substrate or even zero thickness in the impact region of the electron beam(s). In some embodiments, the anodes (with or without the substrate) of the sub-sources are supported on a support frame with an opening reasonably larger than the incident electron beam or x-ray source size. The support frame may have high thermal conductivity and may be cooled using techniques known to those skilled in the art. It is preferred to cool the frame to a temperature down to minus 90° centigrade when the substrate or the frame is made of diamond to make use of the increased thermal conductivity of diamond with decreasing temperature.

The selection of the materials of the linear accumulation source target used in some embodiments is such that the substrate (the first material) is of low Z material with high thermal conductivity, such as diamond or beryllium, and the material of the sub-sources (the second material) are selected for x-ray generating properties such as spectral characteristics and x-ray production efficiency and may include (but are not limited to) copper, molybdenum, and tungsten. In some embodiments, the thermal conductivity of the targets is mainly determined by the thermal conductivity of the substrate material, which allows the use of x-ray generating materials with lower thermal conductivity otherwise not suitable as x-ray target materials, such as germanium and lead, in conventional contiguous single material targets, consequently allowing a greater number of elements available to produce characteristic x-ray lines.

Systems are generally designed such that the all materials in the x-ray beam path from the source to the sample, including the x-ray generating material and the substrate material, should contain no or negligible amounts of elements that absorb x-rays in the spectral region of interest, especially for EXAFS measurement. Multiple x-ray generating materials made may be selected to cover a predetermined x-ray energy range.

The anode targets as shown in FIGS. 1 through 9 may be cooled using methods known in the art, such as water cooling, thermoelectric cooling, and/or heat pipes, which may also be employed to increase the thermal performance of the anode and thus the brightness of the x-ray source.

Any number of prior art techniques for generating electron beams may be used for the embodiments of the linear attenuation x-ray source disclosed herein. Some of the known techniques used for electron beam generation include heating a filament for thermionic emission, Schottky emission (a combination of heating and field emission), emitters comprising nanostructures such as carbon nanotubes), and by use of ferroelectric materials. [For more on electron emission options for electron beam generation, see Shigehiko Yamamoto, "Fundamental physics of vacuum electron sources", Reports on Progress in Physics vol. 69, pp. 181-232 (2006)]. It is preferred that the size of the electron beam is optimized according to the x-ray source size desired.

In some embodiments of the invention, there may also be electron optical systems that in addition to providing electron beam(s) with predetermined property (electron energy, current, and focal spot size), can control and direct the respective electron beams to their desired positions on the respective x-ray targets.

X-Ray Optical Train.

Various embodiments of the x-ray absorption spectroscopy system comprise an x-ray optical train to collect a portion of x-rays from the linear accumulation x-ray source and subsequently spectrally filter, collimate or focus the x-rays to produce an x-ray beam to be incident on the sample to be analyzed. It should be noted that in the variations of optical trains illustrated as cross-sections in the following figures that the optics may be axially symmetric and also have either an absorbing beam stop, slit, or aperture that absorbs x-rays that are not reflected. However, other designs of x-ray optical trains may be known to those skilled in the art.

Optical trains such as those that may be used in embodiments of the invention disclosed herein have been described in detail in the co-pending US Patent Application entitled X-RAY ILLUMINATORS WITH HIGH FLUX AND HIGH FLUX DENSITY (U.S. patent application Ser. No. 14/544,191, filed Dec. 5, 2014), which, along with the provisional Applications incorporated therein and to which it claims benefit (Application Nos. 61/912,478, filed on Dec. 5, 2013, 61/912,486, filed on Dec. 5, 2013, 61/946,475, filed on Feb. 28, 2014, and 62/008,856, filed on Jun. 6, 2014), is hereby incorporated by reference in its entirety.

To improve the numerical aperture of the optical elements of the optical train, some embodiments of the invention may use coatings on the reflective surface. These coatings are preferably high density materials (greater than 2.5 g/cm³) such as platinum, iridium, or gold and typically around a few angstroms to a few nanometers in thickness. Such high density coatings provide a larger critical angle for reflection, enabling the collection of more x-rays. Alternatively, multilayer coatings that reflect x-rays using alternating periodic layers of two or more materials which provide constructive interference in reflection for certain wavelengths. The reflection efficiency depends on the wavelength and angle of incidence of the x-rays, and the thickness of the alternating layers, so this has limited use as a broadband reflector, but may be used if specific wavelengths are desired. Combinations that may be used for multilayer reflectors are tungsten/carbon (W/C), tungsten/tungsten silicide (W/WSi2), molybdenum/silicon (Mo/Si), nickel/carbon (Ni/C), chromium/scandium (Cr/Sc), and lanthanum/boron carbide (La/B$_4$C), and tantalum/silicon (Ta/Si), among others. The surface may also be a compound coating comprising an alloy or mixture of several materials.

In some embodiments, the optics may furthermore be nested (concentric within each other) to allow greater collection of x-rays, as is typical with the non-axial symmetric mirrors used commonly in x-ray astronomy.

Figure 10:
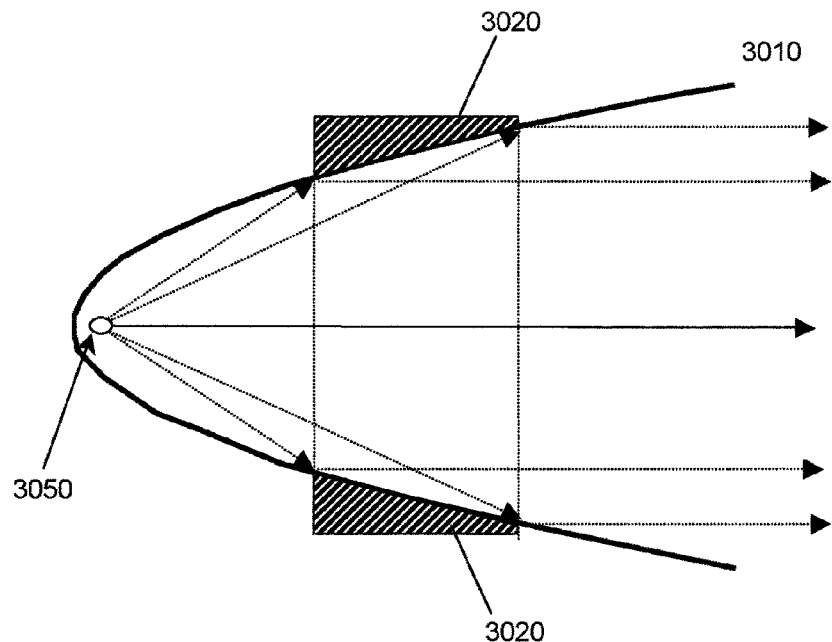
FIG. 10 illustrates a cross section of a paraboloidal optical element.
Figure 11:
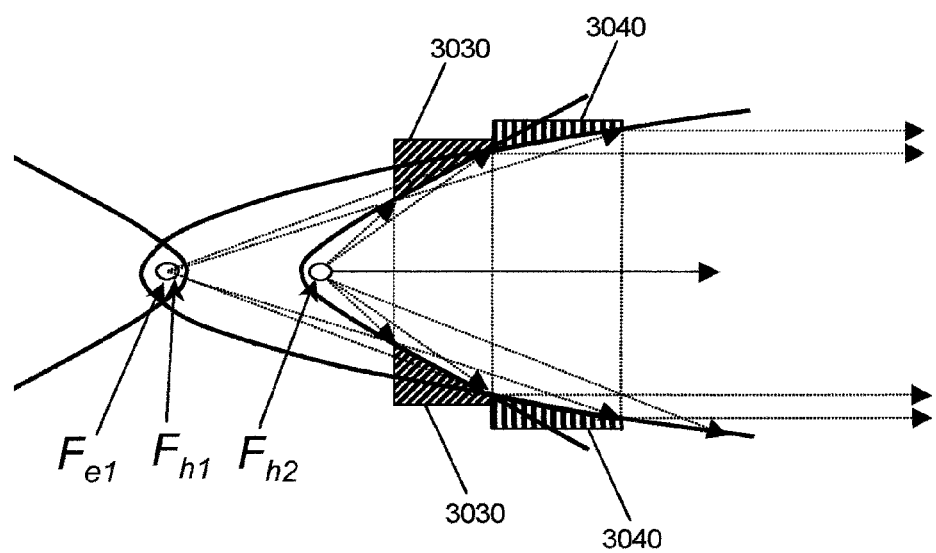
FIG. 11 illustrates a cross section of a type I Wolter optical element.

FIGS. 10 and 11 schematically illustrate variations of optical train components to produce a collimated high brightness x-ray beam. FIG. 10 illustrates a cross-section of an x-ray mirror 3020 of which the interior reflecting surface corresponds to a portion of a paraboloid 3010. It will be generally configured so that its focus 3050 will be positioned with the center of the linear accumulation x-ray source, and that its axis is aligned along the axis of the linear accumulation x-ray source, such as was illustrated by the axis 3000 in FIG. 4. The x-ray mirror 3020 collects x-rays from the source and generates a collimated x-ray beam. As the source will not be a perfect point source, the angular convergence of the collimated beam is approximately equal to the apparent linear accumulation x-ray source divided by the distance between the source and the entrance of the x-ray mirror 3020.

The surface profile of the x-ray mirror may be designed such that the x-rays with the desired x-ray energy incident on the x-ray mirror surface at a grazing angle smaller than or equal to the critical angle for total reflection of the mirror surface material at the desired x-ray energy. The mirror surface material may be glass, or coated either with a high mass density material to increase the critical angle for total reflection to collect more x-rays from the linear accumulation x-ray source. The mirror surface may also be coated with a multilayer of appropriate material composition, d-spacing gradient, and appropriate d-spacing gradient along the optical axis, to increase solid angle of x-ray collection from the linear accumulation x-ray source and obtain an x-ray beam with narrow spectra.

FIG. 11 schematically illustrates a cross-section of another optical train that may be used in embodiments of the presentation invention to produce a collimated high brightness x-ray beam. The optical train in this example comprises a type I Wolter reflecting optic having a first component 3030 corresponding to a hyperboloid and a second component 3040 corresponding to an ellipsoid. Both components are aligned to be co-axial, and with one of the foci of the ellipse $F_{el}$ corresponding to one of the foci of the hyperbola $F_{hl}$.

In embodiments of the invention, the type I Wolter mirror is typically configured such that the focus $F_{hl}$ will be positioned at the center of the linear accumulation x-ray source and its optical axis is aligned to correspond to the axis of the linear accumulation x-ray source, such as was illustrated by the axis 3000 in FIG. 4. Similar to the parabolic optic of FIG. 10, it is preferred that the angular convergence of the collimated beam in the scattering plane is smaller than the critical angle of the sample.

The slopes and surface profiles of the x-ray optics are designed such that the x-rays with the desired x-ray energy are incident on the x-ray mirror surface at a grazing angles that are smaller than or equal to the critical angle of the mirror surface material for total at the desired x-ray energy. The surface material of one or both mirror components may be glass, or coated either with a high mass density material to increase the critical angle for total reflection, which is proportional to the square root of the density of the material. The mirror surface may also be coated with a multilayer of appropriate material composition, d-spacing gradient, and appropriate d-spacing gradient along the optical axis, to increase solid angle of x-ray collection from the linear accumulation x-ray source and obtain an x-ray beam with narrow spectra. Compared with the single paraboloid mirror illustrated in FIG. 10, the type I Wolter mirror illustrated in FIG. 11 can have up to 4× the solid angle of collection of x-rays from the linear accumulation x-ray source, resulting in a collimated x-ray beam with a larger x-ray flux.

The x-ray optical train may further comprise a spectral filtering component to narrow the energy spectra of the collimated x-ray known in the prior art, such as a thin foil spectral filter. Additionally, it may also compromise aperture(s) or slit(s) to obtain a desired beam shape and size, as will be known by those skilled in the art.

In addition to collimating optics, variations of optics for the optical train of embodiments may also use focusing optics. It should be noted that, like the collimating optics, all optical mirror surface materials may be glass, or coated either with a high mass density material. The mirror surface may also be coated with a multilayer of appropriate material composition, d-spacing gradient, and appropriate d-spacing gradient along the optical axis, to increase solid angle of x-ray collection from the linear accumulation x-ray source and obtain an x-ray beam with narrow spectra.

Figure 12:
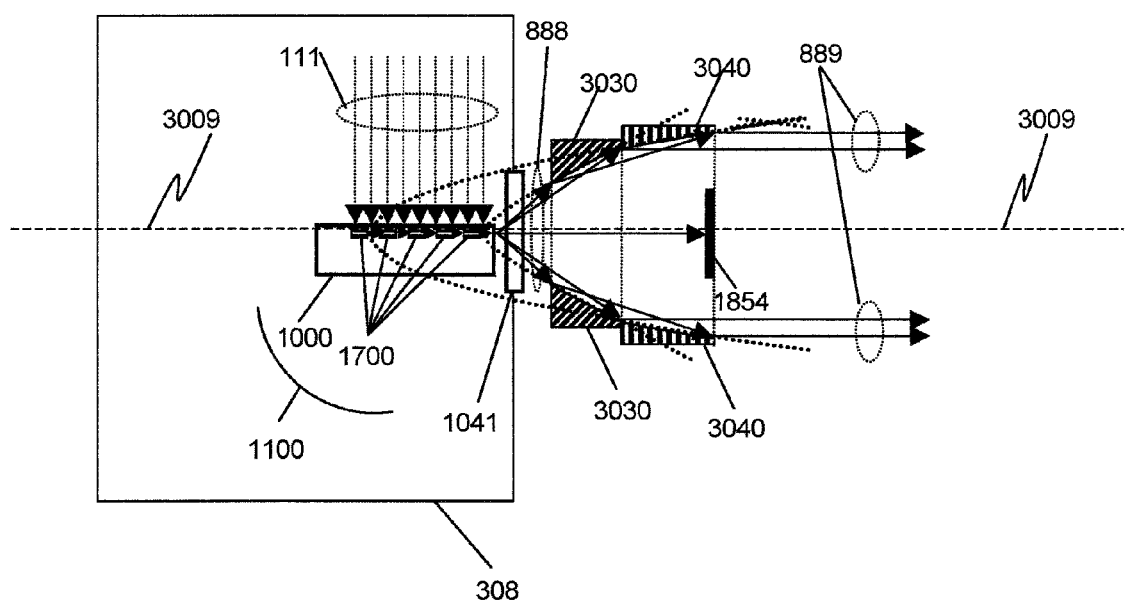
FIG. 12 schematically illustrates a cross sectional view of an x-ray source and a type I Wolter imaging optic as used in some embodiments of the invention.

FIG. 12 illustrates a portion of an embodiment of the invention comprising an x-ray source 308 that uses a target 1100 comprising a substrate 1000 and a plurality of microstructures 1700 that are bombarded by electrons 111 to generate high brightness x-rays 888. These x-rays exit the source through a window 1041 and enter an optical train comprising optical elements 3030 and 3040 in the form of type I Wolter optics aligned along the same axis 3009 that corresponds to the axis of linear accumulation of x-rays in the source 308. The optical train as shown also comprises a beam stop 1854, so that the output of the optical train is a collimated x-ray beam 889.

Compared with the single paraboloid mirror illustrated in FIG. 10, the type I Wolter mirror can have up to 4× solid angle of collection of x-rays from the linear accumulation x-ray source, resulting in a collimated x-ray beam with a larger x-ray flux. Although the optics shown in FIG. 12 are type I Wolter optics, other optical elements such as paraboloidal optical elements or polycapillary optics may be used in similar embodiments of the invention if their configuration produces a collimated or near collimated beam.

The surface profiles of the x-ray mirrors may be designed such that the x-rays with the desired x-ray energy incident on the x-ray mirror surface at a grazing angle smaller than or equal to the critical angle for total reflection of the mirror surface material at the desired x-ray energy. The mirror surface material may be glass, or coated either with a high mass density material to increase the critical angle for total reflection to collect more x-rays from the linear accumulation x-ray source.

X-Ray Monochromator.

As was illustrated in FIG. 3, once a collimated x-ray beam has been created, the collimated x-ray beam enters a monochromator to reduce the energy bandwidth. One example typically used is the double crystal monochromator. The double crystal monochromator can be any number of monochromators known in the art. The double crystal monochromator can comprise two individual single crystals aligned with their respective diffraction planes parallel to each other. Alternatively, it may be a channel cut monochromator created using a monolithic single crystal. Suitable crystal materials include silicon (Si), germanium (Ge), lithium fluoride (LiF), and indium antimonide (InSb). Suitable crystal diffraction plane for a predetermined spectral bandwidth over predetermined energy spectra range can be selected using known art.

Figure 13:
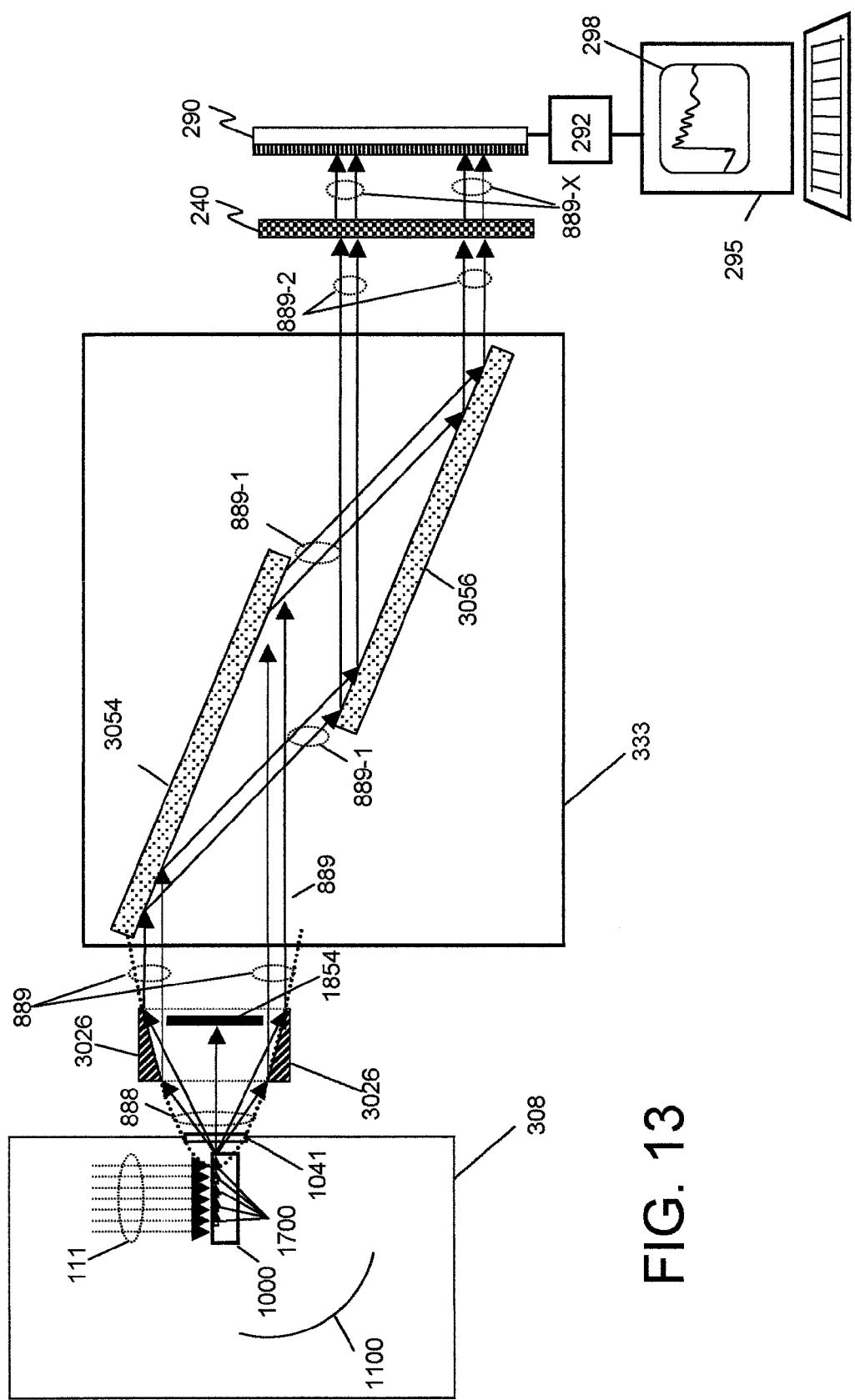
FIG. 13 schematically illustrates a cross-section of a portion of an embodiment of the invention having a double crystal monochromator.

FIG. 13 schematically illustrates an embodiment of the invention to perform XAFS for a sample 240. As in FIG. 12, The x-ray absorption spectroscopy apparatus comprises a linear accumulation x-ray source 308 generating high brightness x-rays 888 using bombardment with electrons 111 of a target 1100 comprising a substrate 1000 with a plurality of microstructures 1700 comprising x-ray generating material. As shown, the x-rays 888 exit the x-ray source 308 through an x-ray window 1041, and the origin of the x-ray generation occurs along a predetermined axis coincident with the axis of a first paraboloidal x-ray mirror 3026, which is properly positioned and aligned to produce a collimated x-ray beam 889. Although a paraboloidal reflecting optic is shown, the optic may alternatively comprise type I Wolter optics, as was shown in FIG. 12, or any number of other x-ray optical elements that can produce a collimated x-ray beam 889. Also, as was shown in FIG. 12, the optical train may comprise a beam stop 1854, so that the output of the optical train is a collimated x-ray beam 889.

The collimated x-ray beam 889 then enters a double crystal monochromator 333 comprising a first crystal 3054, which reflects the desired spectral component 889-1 onto a second crystal 3056 to further limit the spectral bandwidth to produce a monochromatized x-ray beam 889-2 with predetermined x-ray energy. The crystal monochromator may be of any type known to the art, such as common U-shaped (channel-cut) crystals comprised of silicon (Si) or germanium (Ge) single crystal or parallel semiconductor crystal plates. The double crystal monochromator is rotated to change the Bragg angle of the collimated x-ray beam, which enables selection of x-ray energies of interest by changing Bragg angle. The surface material of one or both mirror components may be glass, or coated either with a high mass density material to increase the critical angle for total reflection to collect more x-rays from the linear accumulation x-ray source. It is important that the material of the reflecting surface doesn't contain elements with x-ray absorption edges in the x-ray spectra of interest for a given measurement.

It should be noted that both the angular convergence $\Delta\theta_2$ and the x-ray source size $S_2$ in the out-plane direction can preferably be large to obtain large x-ray flux according to Eqn. 1 without affecting the energy spectral bandwidth of the double crystal monochromator. The surface profiles of the x-ray mirrors are designed such that the x-rays with the desired x-ray energy incident on the x-ray mirror surface at a grazing angle smaller than or equal to the critical angle for total reflection of the mirror surface material at the desired x-ray energy. The mirror surface material may be glass, or coated either with a high mass density material to increase the critical angle for total reflection to collect more x-rays from the linear accumulation x-ray source.

Detection and Analysis.

As shown in FIG. 13, after exiting the monochromator 333, the monochromatic x-ray beam 889-2 in some embodiments of the invention will be directed directly onto the sample 240 to be examined. The transmitted x-rays 889-X then fall onto a detector 290 that detects the x-rays and converts them into electrical signals. These electrical signals then undergo signal processing by signal processing electronics 292, and then undergo further analysis in an analysis system 295 which may also have a display 298 to show the results.

A partially transmissive detector (not shown) may be placed in front of the sample 240 to measure the x-ray beam incident upon the sample, or the sample may be attached to an electromechanical stage that moves the sample out of the beam to measure the incident x-ray beam and then back into the beam to measure the transmitted x-ray beam. In some embodiments, an additional optical train, filter and/or monochromator may be placed after the sample but before the detector to remove background x-rays and improve signal to noise.

Motion of the elements of the optical train, the monochromator 333, and the stage holding the sample 240 may be coordinated to allow the electronic signals correlated with a particular x-ray energy setting to be determined. Multiple datapoints at multiple settings may also be collected to provide an XAFS spectrum.

In various embodiments, the x-ray detector 290 may include a gas filed proportional counter, an ionization chamber, a silicon drift detector, and other x-ray detectors known in art to detect the intensity of the x-rays transmitted through the sample as a function of the monochromatic x-ray energy. Additionally, a spectrometer such as a silicon drift detector may be used to also detect fluorescent x-rays from the sample as a function of the monochromatic x-ray energy Other variations also exist for embodiments of the invention. Additional spectral filters or monochromators may be used between the sample 240 and the detector 290 to select a certain portion of the x-rays emerging from the sample 240 for detection. This may be especially useful if there is a significant amount of x-ray fluorescence from the sample 240 that may interfere with the signals generated by the transmitted x-rays. Alternatively, a second detector, as was illustrated in FIG. 3, may be included to detect the fluorescence directly, either on the back side of the sample 240, or from the front side (before the x-ray beam passes through the sample). Depending on the material under investigation and the spectrum under investigation, such a fluorescence monitor may also serve as an independent monitor for the incident x-ray intensity.

Figure 14:
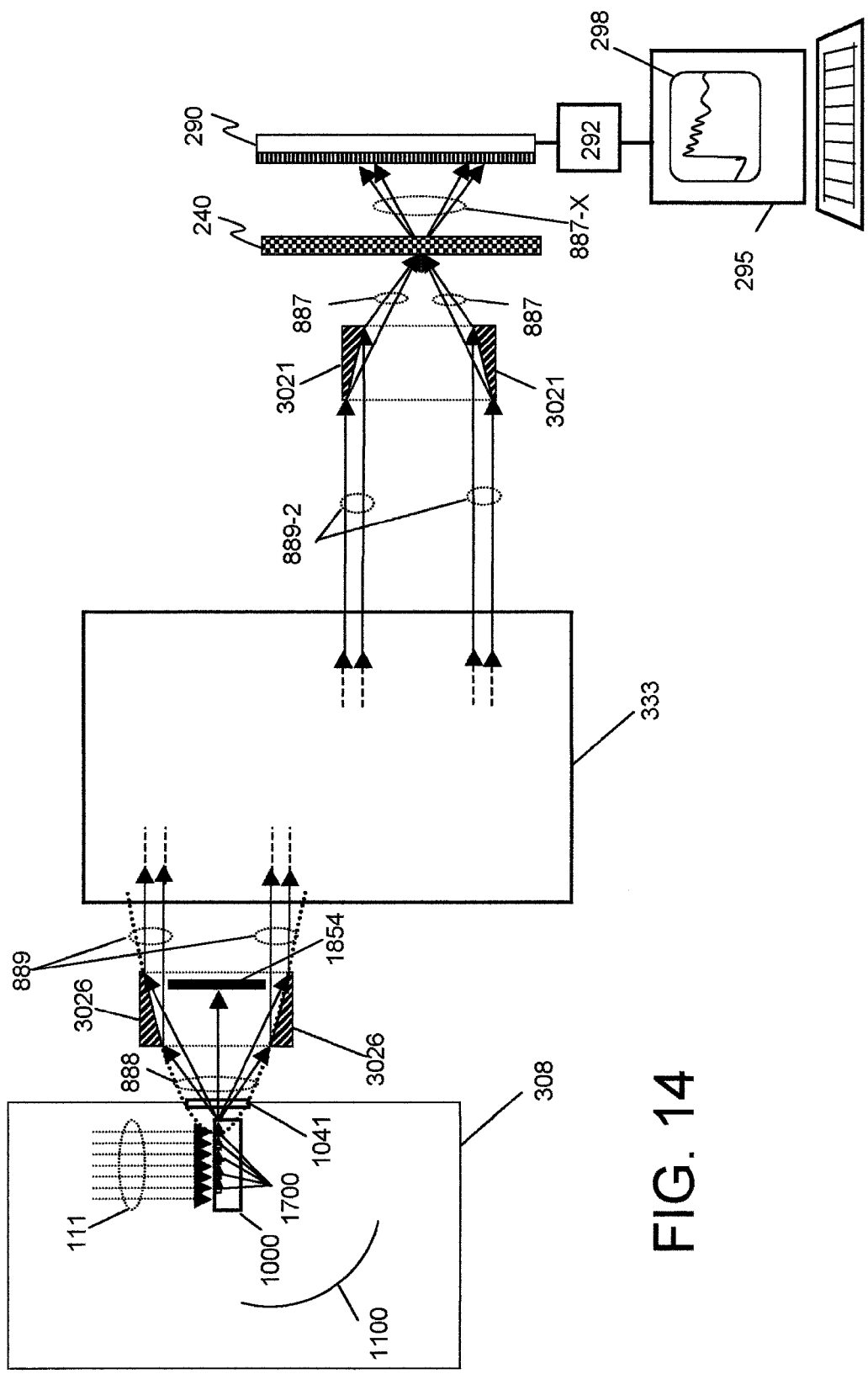
FIG. 14 schematically illustrates a cross-section of a portion of an embodiment of the invention having additional optical elements focus x-rays onto a sample.

FIG. 14 illustrates a variation in which an additional focusing optic 3021 is provided after the monochromator 333 to convert a collimated beam 889-2 into a converging x-ray beam 887. This allows the x-ray transmission of a particular location on the sample 240 to be probed, which may be desired if there is some variation in composition and surface quality present. Likewise, translation of the sample when used with a focused monochromatic x-ray beam may provide information about the micro-composition of the sample.

To keep a fixed position of the focused x-ray beam on the sample, the double crystal monchromator can be designed in accordance with monochromators widely used in synchrotron x-ray absorption spectroscopy facilities. Alternatively, when a channel-cut double crystal monochromator is used, the sample can be moved by an electromechanical system to keep the focused x-ray beam position fixed on the same spot on the sample.

LIMITATIONS AND EXTENSIONS

With this application, several embodiments of the invention, including the best mode contemplated by the inventors, have been disclosed. It will be recognized that, while specific embodiments may be presented, elements discussed in detail only for some embodiments may also be applied to others. Elements in the co-pending Applications incorporated by reference into this Application may also be incorporated into embodiments of the invention disclosed herein.

While specific materials, designs, configurations have been set forth to describe this invention and the preferred embodiments, such descriptions are not intended to be limiting. Modifications and changes may be apparent to those skilled in the art, and it is intended that this invention be limited only by the scope of the appended claims.

We claim:

1. An x-ray absorption measurement system, comprising:
an x-ray source comprising:
a vacuum chamber;
a window transparent to x-rays attached to the wall of the vacuum chamber;
and, within the vacuum chamber:
at least one electron beam emitter, and
an anode target comprising:
 a substrate comprising a first selected material, and
 a planar first surface, from which thickness is measured in a direction perpendicular to the first planar surface, and
 two orthogonal lateral dimensions are measured parallel to the first planar surface; and
a plurality of discrete structures embedded into the first planar surface of the substrate such that each of the plurality of discrete structures is in thermal contact with the substrate, the plurality of discrete structures comprising:
 one or more materials selected for its x-ray generation properties;
in which at least two of the plurality of discrete structures are arranged on an axis;
in which the axis is parallel to the first planar surface of the substrate;
in which the axis passes through the first window;
 in which each of the discrete structures has a thickness of less than 20 microns, and
 in which each of the plurality of discrete structures has a lateral dimension in the direction of the axis of less than 50 microns; and
a means of directing electrons emitted by the at least one electron beam emitter onto the at least two arranged discrete structures such that x-rays are generated from each of the at least two arranged discrete structures;
in which at least a portion of the generated x-rays propagating on the axis from each of the two arranged discrete structures is transmitted through the window; and
said system further comprising:
an optical train having an optical axis positioned to correspond to the axis on which the at least two discrete structures are arranged;
in which the optical train is further positioned to collect x-rays generated by the anode target and produce an x-ray beam with predetermined beam properties;
a monochromator to select x-rays of a predetermined energy and bandwidth from the x-ray beam, and additionally having the capability of scanning the selected x-rays over a predetermined energy range;
a mount to hold an object to be investigated positioned such that the x-rays emerging from the monochromator will be incident on the object; and
a detector to measure x-rays transmitted through the object.

2. The system of claim 1, additionally comprising:
a detector to measure the intensity of the x-rays incident on the object.

3. The system of claim 1, additionally comprising:
a detector to measure the intensity of x-ray fluorescence emitted by the object when exposed to the x-rays of a predetermined energy and bandwidth.

4. The system of claim 1, in which
the mount has controls to adjust the position and rotation of the object to be investigated; and
additionally comprising:
a control system to coordinate one or more settings of the monochromator as well as the position and rotation of the object.

5. The system of claim 1, in which
the plurality of discrete structures are arranged in a linear array along said axis; and
the optical train is also aligned along said axis.

6. The system of claim 1, in which
the first selected material is selected from the group consisting of:
beryllium, diamond, graphite, silicon, boron nitride, silicon carbide, sapphire, and diamond-like carbon.

7. The system of claim 1, in which
the one or more materials selected for its x-ray generation properties is selected from the group consisting of:
aluminum, titanium, vanadium, chromium, manganese, iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead, and combinations and alloys thereof.

8. The system of claim 1, comprising:
one or more additional discrete structures embedded into the first planar surface of the substrate comprising an additional material selected for its x-ray generation properties.

9. The system of claim 8, in which
the additional material is selected from the group consisting of:
aluminum, titanium, vanadium, chromium, manganese, iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead, and combinations and alloys thereof.

10. The system of claim 1, in which
the plurality of discrete structures are arranged such that x-rays generated by a predetermined number of the plurality of discrete structures when exposed to an electron beam from the electron beam emitter are transmitted through a predetermined one of the discrete structures selected from the plurality of discrete structures.

11. The system of claim 1, in which the optical train comprises an x-ray reflector with a surface corresponding to a quadric surface.

12. The system of claim 11, in which the quadric surface is selected from the group consisting of: a spheroid, an ellipsoid, a paraboloid, a hyperboloid, an elliptic cylinder, a circular cylinder, an elliptic cone, and a circular cone.

13. The system of claim 1, in which the optical train comprises a type I Wolter x-ray optic.

14. The system of claim 1, in which the x-rays emerging from the monochromator have a predetermined energy bandwidth that is less than 10 eV.

15. The system of claim 14, in which the predetermined energy bandwidth is less than 1 eV.

16. The system of claim 1, in which the monochromator comprises a channel cut crystal comprising a material selected from the group consisting of: silicon, germanium, lithium fluoride, and indium antimonide.

17. The system of claim 1, in which the monochromator comprises a double crystal monochromator.

18. The system of claim 1, in which the plurality of discrete structures comprises three or more structures.

19. The system of claim 1, in which the optical train comprises one or more x-ray optical components that are axially symmetric.

20. The system of claim 1, additionally comprising: an x-ray focusing optical element positioned between the monochromator and the mount.

21. An x-ray absorption measurement system, comprising:
a plurality of electron emitters and a plurality of anode targets, in which each anode target comprises a material selected for its x-ray generation properties;
said emitters and targets positioned such that each electron emitter is aligned to provide an electron beam to bombard a corresponding anode target to generate x-rays, and
the anode targets are aligned such that the positions at which x-rays are generated are aligned along a predetermined axis; and
at least one x-ray imaging optic, in which said x-ray imaging optic is positioned between an adjacent pair of the anode targets such that the x-ray imaging optic collects x-rays radiated from one of the targets of the pair and focuses the collected x-rays onto the other target of the pair;
said system further comprising:
an optical train, in which a portion of the optical train is also aligned along said predetermined axis, and is configured to collect x-rays generated by the anode target and produce an x-ray beam with predetermined beam properties;
a monochromator to select x-rays of a predetermined energy and bandwidth from the x-ray beam, and additionally having the capability of scanning the selected x-rays over a predetermined energy range;
a mount to hold an object to be investigated positioned such that the x-rays emerging from the monochromator will be incident on the object; and
a detector to measure x-rays transmitted through the object.

22. The system of claim 21, in which said at least one x-ray imaging optic comprises a reflecting surface with a quadric profile.

23. The system of claim 22, in which the quadric profile is a paraboloidal profile.

24. The system of claim 21, in which said at least one x-ray imaging optic has at least one reflecting surface with at least one additional coating of a high density material.

25. The system of claim 21, in which said at least one x-ray imaging optic has an optical axis, and
said optical axis is aligned with said predetermined axis; and
said optic is aligned to collect x-rays radiated from one of the targets of the pair and forms an image of said one of the targets onto said other target of the pair.

26. The system of claim 21, in which at least one of the plurality of anode targets comprises a substrate with at least two opposite sides, and each of the two opposite sides has a structure comprising a material selected for its x-ray generation properties in which at least one dimension of the structure is less than 20 micrometers;
and, among the plurality of electron emitters, one electron emitter is aligned to provide an electron beam to bombard the structure on one side of said one of the plurality of anode targets, and another electron emitter is aligned to provide an electron beam to bombard the structure on the opposite side of said one of the plurality of anode targets.

27. The system of claim 26, in which the substrate comprises a material selected from the group consisting of:
beryllium, diamond, graphite, silicon, boron nitride, silicon carbide, sapphire, and diamond-like carbon.

28. The system of claim 26, in which the material selected for its x-ray generation properties is selected from the group consisting of:
aluminum, titanium, vanadium, chromium, manganese, iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead, and combinations and alloys thereof.

29. The system of claim 21, in which at least one of the plurality of anode targets, comprises a plurality of discrete microstructures comprising a material selected for its x-ray generation properties;
in which at least one of the discrete microstructures has at least one dimension of less than 20 microns.

30. The system of claim 29, in which the material selected for its x-ray generation properties is selected from the group consisting of:
aluminum, titanium, vanadium, chromium, manganese, iron, cobalt, nickel, copper, gallium, zinc, yttrium, zirconium, molybdenum, niobium, ruthenium, rhodium, palladium, silver, tin, iridium, tantalum, tungsten, indium, cesium, barium, gold, platinum, lead, and combinations and alloys thereof.

* * * * *